(12) United States Patent
Freier et al.

(10) Patent No.: US 7,176,303 B2
(45) Date of Patent: Feb. 13, 2007

(54) MODULATION OF STAT5 EXPRESSION

(75) Inventors: Susan M. Freier, San Diego, CA (US); James Karras, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 15 days.

(21) Appl. No.: 10/704,263

(22) Filed: Nov. 6, 2003

(65) Prior Publication Data

US 2005/0101013 A1     May 12, 2005

(51) Int. Cl.
    *C07H 21/04* (2006.01)
(52) U.S. Cl. ............... 536/24.5; 435/5; 435/6; 435/91.2; 536/23.1; 536/24.3; 536/24.31; 536/24.33
(58) Field of Classification Search ........... 536/23.1, 536/24.5, 24.3, 24.31, 24.33
    See application file for complete search history.

(56) References Cited

U.S. PATENT DOCUMENTS

| 5,534,409 | A |   | 7/1996 | Groner et al. |
| 5,618,693 | A |   | 4/1997 | McKnight et al. |
| 5,801,154 | A | * | 9/1998 | Baracchini et al. ............ 514/44 |
| 5,955,276 | A | * | 9/1999 | Morgante et al. ............... 435/6 |
| 5,998,148 | A | * | 12/1999 | Bennett et al. ................. 435/6 |
| 6,160,092 | A |   | 12/2000 | Chen et al. |
| 6,444,464 | B1 | * | 9/2002 | Wyatt .......................... 435/375 |
| 6,518,021 | B1 |   | 2/2003 | Thastrup et al. |
| 2003/0105057 | A1 |   | 6/2003 | Fu et al. |

FOREIGN PATENT DOCUMENTS

| WO | WO 92/05284 | * | 4/1992 |
| WO | WO 01/05832 | * | 1/2001 |
| WO | WO 02/46466 |   | 6/2002 |

OTHER PUBLICATIONS

Leong et al. Differential function of STAT5 isoforms in head and neck cancer growth control. Oncogene 2002, vol. 21, 2846-2853. Nature Publishing Group.*
Ahonen et al., Inhibition of transcription factor Stat5 induces cell death of human prostate cancer cells, *J. Biol. Chem.*, 2003.
Ambrosio et al., The structure of human STAT5A and B genes reveals two regions of nearly identical sequence and an alternative tissue specific STAT5B promoter, *Gene*, 2002, 285:311-318.
Arnould et al., The signal transducer and activator of transcription STAT5b gene is a new partner of retinoic acid receptor alpha in acute promyelocytic-like leukaemia, *Hum. Mol. Genet.*, 1999, 8:1741-1749.
Azam et al., Functionally distinct isoforms of STAT5 are generated by protein processing, *Immunity*, 1997, 6:691-701.
Baskiewicz-Masiuk et al., The Role Of STAT5 Proteins In the Regulation Of Normal Hematopoiesis In A Cord Blood Model, *Cell Mol. Biol. Lett.*, 2003, 8:317-331.
Bromberg, Stat proteins and oncogenesis, *J. Clin. Invest.*, 2002, 109:1139-1142.
Carlesso et al., Tyrosyl phosporylation and DNA binding activity of signal transducers and activators of transcription (STAT) proteins in hematopoietic cell lines transformed by Bcr/Abl, *J. Exp. Med.*, 1996, 183:811-820.
Chai et al., Constitutive activation of JAKs and STATs in BCR-Abl-expressing cell lines and peripheral blood cells derived from leukemic patients, *J. Immunol.*, 1997, 159:4720-4728.
Coffer et al., The role of STATs in myeloid differentiation and leukemia, *Oncogne*, 2000, 19:2511-2522.
de Groot et al., STAT5 activation by BCR-Abl contributes to transformation of K562 leukemia cells, *Blood*, 1999, 94:1108-1112.
Demoulin et al., Distinct roles for STAT1, STAT3, and STAT5 in differentiation gene induction and apoptosis inhibition by interleukin-9, *J. Biol. Chem.*, 1999, 274:25855-25861.
Donato et al., Down-regulation of interleukin—3/granulocyte-macrophage colony-stimulating factor receptor beta-chain in BCR-ABL (+) human leukemic cells: association with loss of cytokine-mediated Stat-5 activation and protection from apoptosis after BCR-ABL inhibition, *Blood*, 2001, 97:2846-2853.
Dong et al., Interactions of STAT5b-RARalpha, a novel acute promyelocytic leukemia fusion protein, with retinoic acid receptor and STAT3 signaling pathways, *Blood*, 2002, 99:2637-2646.
Gouilleux-Gruart et al., STAT-related transcription factors are constitutively activated in peripheral blood cells from acute leukemia patients, *Blood*, 1996, 87:1692-1697.
Grimley et al., Stat5a and Statb: fraternal twins of signal transduction and transcriptional activation, *Cytokine Growth Factor Rev.*, 1999, 10:131-157.

(Continued)

*Primary Examiner*—Sean McGarry
*Assistant Examiner*—Kimberly Chong
(74) *Attorney, Agent, or Firm*—Knobbe, Martens, Olson and Bear, LLP

(57) ABSTRACT

Compounds, compositions and methods are provided for modulating the expression of STAT5. The compositions comprise oligonucleotides, targeted to nucleic acid encoding STAT5. Methods of using these compounds for modulation of STAT5 expression and for diagnosis and treatment of diseases and conditions associated with expression of STAT5 are provided.

8 Claims, No Drawings

OTHER PUBLICATIONS

Hou et al., Indentification and purification of human Stat proteins activated in response to interleukin-2, *Immunity*, 1995, 2:321-329.

Huang et al., Inhibition of Bcr-Abl kinase activity by PD180970 blocks constitutive activation of Stat5 and growth of CML cells, *Oncogene*, 2002, 21: 8804-8816.

Kazansky et al., Regulation of mammary gland factor/Stat5a during mammary gland development, *Mol. Endocrinol.*, 1995, 9:1598-1609.

Leong et al., Differential function of STAT5 isoforms in head and neck cancer growth control, *Oncogene*, 2002, 21:2846-2853.

Lin et al., STAT signaling in the pathogenesis and treatment of leukemias, *Oncogene*, 19:2496-2504.

Lin et al., Cloning of human Stat5B. Reconstitution of interleukin-2-induced Stat5A and Stat5B DNA binding activity in COS-7 cells, *J. Biol. Chem.*, 1996, 271:10738-10744.

Liu et al., Cloning and expression of Stat5 and an additional homologue (Stat5b) involved in prolactin signal transduction in mouse mammary tissue, *Proc. Natl. Acad. Sci. U S A*, 1995, 92:8831-8835.

Liu et al., Stat5a is mandatory for adult mammary gland development and lactogenesis, *Genes Dev.*, 1997, 11:179-186.

Moriggl et al., Deletion of the carboxyl-terminal transactivation domain of MGF-Stat5 results in sustained DNA binding and a dominant negative phenotype, *Mol. Cell. Biol.*, 1996, 16:5691-5700.

Ripperger et al., Transcription factors Stat3 and Stat5b are present in rat liver nuclei late in an acute phase response and bind interleukin-6 response elements, *J. Biol. Chem.*, 1995, 270:29998-30006.

Shuai et al., Constitutive activation of STAT5 by the BCR-ABL oncogene in chronic myelogenous leukemia, *Oncogene*, 1996, 13:247-254.

Spiekermann et al., Overexpression and Constitutive Activation of FLT3 Induces STAT5 Activation in Primary Acute Myeloid Leukemia Blast Cells, *Clin. Cancer Res.*, 2003, 9:2140-2150.

Spiekermann et al., Constitutive activation of STAT3 and STAT5 is induced by leukemic fusion proteins with protein tyrosine kinase activity and is sufficient for transformation of hematopoietic precursor cells, *Exp. Hematol.*, 2002, 30:262-271.

Takemoto et al., Proliferation of adult T cell leukemia/lymphoma cells is associated with the constitutive activation of JAK/STAT proteins, *Proc. Natl. Acad. Sci. U S A*, 1997, 94:13897-13902.

Teglund et al., Stat5a and Stat5b proteins have essential and nonessential, or redundant, roles in cytokine responses, *Cell*, 1998, 93:841-850.

Udy et al., Requirement of STAT5b for sexual dimorphism of body growth rates and liver gene expression, *Proc. Natl. Acad. Sci. U S A*, 1997, 94:7239-7244.

Wakao et al., Mammary gland factor (MGF) is a novel member of the cytokine regulated transcription factor gene family and confers the prolactin response, *Embo J.*, 1994, 13:2182-2191.

Wang et al., Naturally occurring dominant negative variants of Stat5, *Mol. Cell. Biol.*, 1996, 16:6141-6148.

Weber-Nordt et al., Constitutive activation of STAT proteins in primary lymphoid and myeloid leukemia cells and in Epstein-Barr virus (EBV)-related lymphoma cell lines, *Blood*, 1996, 88:809-816.

Xia et al., Expression of signal transducers and activators of transcription proteins in acute myeloid leukemia blasts, *Cancer Res.*, 1998, 58:3173-3180.

Behod et al., Specific Inhibition on Stat5a/b Promtes Apoptosis of IL-2-Responsive Primary and Tumor-Derived Lymphoid Cells, *J of Immunology*, 2003, 171:3919-3927.

* cited by examiner

SEQUENCE LISTING

<160> NUMBER OF SEQ ID NOS: 213

<210> SEQ ID NO 1
<211> LENGTH: 20
<212> TYPE: DNA
<213> ORGANISM: Artificial Sequence
<220> FEATURE:
<223> OTHER INFORMATION: Antisense Compound

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Antisense Compound

<400> SEQUENCE: 2
gtgcgcgcga gcccgaaatc                                              20

<210> SEQ ID NO 3
<211> LENGTH: 20
<212> TYPE: DNA
<213> ORGANISM: Artificial Sequence
<220> FEATURE:
<223> OTHER INFORMATION: Antisense Compound

<400> SEQUENCE: 3
atgcattctg cccccaagga                                              20

<210> SEQ ID NO 4
<211> LENGTH: 4298
<212> TYPE: DNA
<213> ORGANISM: H. sapiens
<220> FEATURE:
<221> NAME/KEY: CDS
<222> LOCATION: (642)...(3026)
<223> OTHER INFORMATION: Antisense compound -continued

```
<400> SEQUENCE: 4
cagacaggat attcactgct gtggcaaggc ctgtagagag tttcgaagtt aggaggactc      60
aagacggtcc ctccctggac ttttctgaag gggctcaaaa gatgacacgc gccagagctg     120
gaaggcgtcg ccaattggtc caacttttcc ctcctccctt tttgcggatg agaaaaactg     180
aggcccaggt ttgggatttc cagagcccgg gatttcccgg caacgccgac aaccacattc     240
ccccggctat tctgacccgc cccggttccg ggacgctccc tgggagccgc cgccgagggc     300
ctgctgggac tcccggggac cccgccgtcg ggcagcccc cacgcccggc gccgcccgcc      360
ggaacggcgc cgctgttgcg cacttgcagg ggagccggcg actgagggcg aggcagggag     420
ggagcaagcg gggctgggag ggctgctggc gcgggctcgc cggctgtgta tggtctatcg     480
caggcagctg acctttgagg aggaaatcgc tgctctccgc tccttcctgt agtaacagcc     540
gccgctgccg ccgccgccag gaaccccggc cgggagcgag agccgcgggg cgcagagccg     600
gcccggctgc cggacggtgc ggccccacca ggtgaacggc c atg gcg ggc tgg atc    656
                                              Met Ala Gly Trp Ile
                                                1               5
cag gcc cag cag ctg cag gga gac gcg ctg cgc cag atg cag gtg ctg       704
Gln Ala Gln Gln Leu Gln Gly Asp Ala Leu Arg Gln Met Gln Val Leu
             10                  15                  20
tac ggc cag cac ttc ccc atc gag gtc cgg cac tac ttg gcc cag tgg       752
Tyr Gly Gln His Phe Pro Ile Glu Val Arg His Tyr Leu Ala Gln Trp
         25                  30                  35
att gag agc cag cca tgg gat gcc att gac ttg gac aat ccc cag gac       800
Ile Glu Ser Gln Pro Trp Asp Ala Ile Asp Leu Asp Asn Pro Gln Asp
     40                  45                  50
aga gcc caa gcc acc cag ctc ctg gag ggc ctg gtg cag gag ctg cag       848
Arg Ala Gln Ala Thr Gln Leu Leu Glu Gly Leu Val Gln Glu Leu Gln
 55                  60                  65
aag aag gcg gag cac cag gtg ggg gaa gat ggg ttt tta ctg aag atc       896
Lys Lys Ala Glu His Gln Val Gly Glu Asp Gly Phe Leu Leu Lys Ile
 70                  75                  80                  85
aag ctg ggg cac tac gcc acg cag ctc cag aaa aca tat gac cgc tgc       944
Lys Leu Gly His Tyr Ala Thr Gln Leu Gln Lys Thr Tyr Asp Arg Cys
                 90                  95                 100
ccc ctg gag ctg gtc cgc tgc atc cgg cac att ctg tac aat gaa cag       992
Pro Leu Glu Leu Val Arg Cys Ile Arg His Ile Leu Tyr Asn Glu Gln
            105                 110                 115
agg ctg gtc cga gaa gcc aac aat tgc agc tct ccg gct ggg atc ctg      1040
Arg Leu Val Arg Glu Ala Asn Asn Cys Ser Ser Pro Ala Gly Ile Leu
        120                 125                 130
gtt gac gcc atg tcc cag aag cac ctt cag atc aac cag aca ttt gag      1088
Val Asp Ala Met Ser Gln Lys His Leu Gln Ile Asn Gln Thr Phe Glu
    135                 140                 145
gag ctg cga ctg gtc acg cag gac aca gag aat gag ctg aag aaa ctg      1136
Glu Leu Arg Leu Val Thr Gln Asp Thr Glu Asn Glu Leu Lys Lys Leu
150                 155                 160                 165
cag cag act cag gag tac ttc atc atc cag tac cag gag agc ctg agg      1184
Gln Gln Thr Gln Glu Tyr Phe Ile Ile Gln Tyr Gln Glu Ser Leu Arg
                170                 175                 180
atc caa gct cag ttt gcc cag ctg gcc cag ctg agc ccc cag gag cgt      1232
Ile Gln Ala Gln Phe Ala Gln Leu Ala Gln Leu Ser Pro Gln Glu Arg
            185                 190                 195
ctg agc cgg gag acg gcc ctc cag cag aag cag gtg tct ctg gag gcc      1280
Leu Ser Arg Glu Thr Ala Leu Gln Gln Lys Gln Val Ser Leu Glu Ala
        200                 205                 210
tgg ttg cag cgt gag gca cag aca ctg cag cag tac cgc gtg gag ctg      1328
Trp Leu Gln Arg Glu Ala Gln Thr Leu Gln Gln Tyr Arg Val Glu Leu
    215                 220                 225
gcc gag aag cac cag aag acc ctg cag ctg ctg cgg aag cag cag acc      1376
Ala Glu Lys His Gln Lys Thr Leu Gln Leu Leu Arg Lys Gln Gln Thr
230                 235                 240                 245
atc atc ctg gat gac gag ctg atc cag tgg aag cgg cgg cag cag ctg      1424
Ile Ile Leu Asp Asp Glu Leu Ile Gln Trp Lys Arg Arg Gln Gln Leu
                250                 255                 260
gcc ggg aac ggc ggg ccc ccc gag ggc agc ctg gac gtg cta cag tcc      1472
Ala Gly Asn Gly Gly Pro Pro Glu Gly Ser Leu Asp Val Leu Gln Ser
            265                 270                 275
tgg tgt gag aag ttg gcc gag atc atc tgg cag aac cgg cag cag atc      1520
Trp Cys Glu Lys Leu Ala Glu Ile Ile Trp Gln Asn Arg Gln Gln Ile
```

-continued

```
                280                 285                 290
cgc agg gct gag cac ctc tgc cag cag ctg ccc atc ccc ggc cca gtg      1568
Arg Arg Ala Glu His Leu Cys Gln Gln Leu Pro Ile Pro Gly Pro Val
            295                 300                 305
gag gag atg ctg gcc gag gtc aac gcc acc atc acg gac att atc tca      1616
Glu Glu Met Leu Ala Glu Val Asn Ala Thr Ile Thr Asp Ile Ile Ser
310                 315                 320                 325
gcc ctg gtg acc agc aca ttc atc att gag aag cag cct cct cag gtc      1664
Ala Leu Val Thr Ser Thr Phe Ile Ile Glu Lys Gln Pro Pro Gln Val
                330                 335                 340
ctg aag acc cag acc aag ttt gca gcc acc gta cgc ctg ctg gtg ggc      1712
Leu Lys Thr Gln Thr Lys Phe Ala Ala Thr Val Arg Leu Leu Val Gly
            345                 350                 355
ggg aag ctg aac gtg cac atg aat ccc ccc cag gtg aag gcc acc atc      1760
Gly Lys Leu Asn Val His Met Asn Pro Pro Gln Val Lys Ala Thr Ile
        360                 365                 370
atc agt gag cag cag gcc aag tct ctg ctt aaa aat gag aac acc cgc      1808
Ile Ser Glu Gln Gln Ala Lys Ser Leu Leu Lys Asn Glu Asn Thr Arg
    375                 380                 385
aac gag tgc agt ggt gag atc ctg aac aac tgc tgc gtg atg gag tac      1856
Asn Glu Cys Ser Gly Glu Ile Leu Asn Asn Cys Cys Val Met Glu Tyr
390                 395                 400                 405
cac caa gcc acg ggc acc ctc agt gcc cac ttc agg aac atg tca ctg      1904
His Gln Ala Thr Gly Thr Leu Ser Ala His Phe Arg Asn Met Ser Leu
                410                 415                 420
aag agg atc aag cgt gct gac cgg cgg ggt gca gag tcc gtg aca gag      1952
Lys Arg Ile Lys Arg Ala Asp Arg Arg Gly Ala Glu Ser Val Thr Glu
            425                 430                 435
gag aag ttc aca gtc ctg ttt gag tct cag ttc agt gtt ggc agc aat      2000
Glu Lys Phe Thr Val Leu Phe Glu Ser Gln Phe Ser Val Gly Ser Asn
        440                 445                 450
gag ctt gtg ttc cag gtg aag act ctg tcc cta cct gtg gtt gtc atc      2048
Glu Leu Val Phe Gln Val Lys Thr Leu Ser Leu Pro Val Val Val Ile
    455                 460                 465
gtc cac ggc agc cag gac cac aat gcc acg gct act gtg ctg tgg gac      2096
Val His Gly Ser Gln Asp His Asn Ala Thr Ala Thr Val Leu Trp Asp
470                 475                 480                 485
aat gcc ttt gct gag ccg ggc agg gtg cca ttt gcc gtg cct gac aaa      2144
Asn Ala Phe Ala Glu Pro Gly Arg Val Pro Phe Ala Val Pro Asp Lys
                490                 495                 500
gtg ctg tgg ccg cag ctg tgt gag gcg ctc aac atg aaa ttc aag gcc      2192
Val Leu Trp Pro Gln Leu Cys Glu Ala Leu Asn Met Lys Phe Lys Ala
            505                 510                 515
gaa gtg cag agc aac cgg ggc ctg acc aag gag aac ctc gtg ttc ctg      2240
Glu Val Gln Ser Asn Arg Gly Leu Thr Lys Glu Asn Leu Val Phe Leu
        520                 525                 530
gcg cag aaa ctg ttc aac aac agc agc agc cac ctg gag gac tac agt      2288
Ala Gln Lys Leu Phe Asn Asn Ser Ser Ser His Leu Glu Asp Tyr Ser
    535                 540                 545
ggc ctg tcc gtg tcc tgg tcc cag ttc aac agg gag aac ttg ccg ggc      2336
Gly Leu Ser Val Ser Trp Ser Gln Phe Asn Arg Glu Asn Leu Pro Gly
550                 555                 560                 565
tgg aac tac acc ttc tgg cag tgg ttt gac ggg gtg atg gag gtg ttg      2384
Trp Asn Tyr Thr Phe Trp Gln Trp Phe Asp Gly Val Met Glu Val Leu
                570                 575                 580
aag aag cac cac aag ccc cac tgg aat gat ggg gcc atc cta ggt ttt      2432
Lys Lys His His Lys Pro His Trp Asn Asp Gly Ala Ile Leu Gly Phe
            585                 590                 595
gtg aat aag caa cag gcc cac gac ctg ctc atc aac aag ccc gac ggg      2480
Val Asn Lys Gln Gln Ala His Asp Leu Leu Ile Asn Lys Pro Asp Gly
        600                 605                 610
acc ttc ttg ctg cgc ttt agt gac tca gaa atc ggg ggc atc acc atc      2528
Thr Phe Leu Leu Arg Phe Ser Asp Ser Glu Ile Gly Gly Ile Thr Ile
    615                 620                 625
gcc tgg aag ttt gac tcc ccg gaa cgc aac ctg tgg aac ctg aaa cca      2576
Ala Trp Lys Phe Asp Ser Pro Glu Arg Asn Leu Trp Asn Leu Lys Pro
630                 635                 640                 645
ttc acc acg cgg gat ttc tcc atc agg tcc ctg gct gac cgg ctg ggg      2624
Phe Thr Thr Arg Asp Phe Ser Ile Arg Ser Leu Ala Asp Arg Leu Gly
                650                 655                 660
gac ctg agc tat ctc atc tat gtg ttt cct gac cgc ccc aag gat gag      2672
Asp Leu Ser Tyr Leu Ile Tyr Val Phe Pro Asp Arg Pro Lys Asp Glu
            665                 670                 675
gtc ttc tcc aag tac tac act cct gtg ctg gct aaa gct gtt gat gga      2720
Val Phe Ser Lys Tyr Tyr Thr Pro Val Leu Ala Lys Ala Val Asp Gly
        680                 685                 690
tat gtg aaa cca cag atc aag caa gtg gtc cct gag ttt gtg aat gca      2768
Tyr Val Lys Pro Gln Ile Lys Gln Val Val Pro Glu Phe Val Asn Ala
    695                 700                 705
```

```
tct gca gat gct ggg ggc agc agc gcc acg tac atg gac cag gcc ccc    2816
Ser Ala Asp Ala Gly Gly Ser Ser Ala Thr Tyr Met Asp Gln Ala Pro
710                 715                 720                 725
tcc cca gct gtg tgc ccc cag gct ccc tat aac atg tac cca cag aac    2864
Ser Pro Ala Val Cys Pro Gln Ala Pro Tyr Asn Met Tyr Pro Gln Asn
                730                 735                 740
cct gac cat gta ctc gat cag gat gga gaa ttc gac ctg gat gag acc    2912
Pro Asp His Val Leu Asp Gln Asp Gly Glu Phe Asp Leu Asp Glu Thr
            745                 750                 755
atg gat gtg gcc agg cac gtg gag gaa ctc tta cgc cga cca atg gac    2960
Met Asp Val Ala Arg His Val Glu Glu Leu Leu Arg Arg Pro Met Asp
        760                 765                 770
agt ctt gac tcc cgc ctc tcg ccc cct gcc ggt ctt ttc acc tct gcc    3008
Ser Leu Asp Ser Arg Leu Ser Pro Pro Ala Gly Leu Phe Thr Ser Ala
    775                 780                 785
aga ggc tcc ctc tca tga atgtttgaat cccacgcttc tctttggaaa           3056
Arg Gly Ser Leu Ser *
790
caatatgcaa tgtgaagcgg tcgtgttgtg agtttagtaa ggttgtgtac actgacacct  3116
ttgcaggcat gcatgtgctt gtgtgtgtgt gtgtgtgtgt gtccttgtgc atgagctacg  3176
cctgcctccc ctgtgcagtc ctgggatgtg gctgcagcag cggtggcctc ttttcagatc  3236
atggcatcca agagtgcgcc gagtctgtct ctgtcatggt agagaccgag cctctgtcac  3296
tgcaggcact caatgcagcc agacctattc ctcctgggcc cctcatctgc tcagcagcta  3356
tttgaatgag atgattcaga aggggagggg agacaggtaa cgtctgtaag ctgaagtttc  3416
actccggagt gagaagcttt gccctcctaa gagagagaga cagagagaca gagagagaga  3476
aagagagagt gtgtgggtct atgtaaatgc atctgtcctc atgtgttgat gtaaccgatt  3536
catctctcag aagggaggct gggggttcat tttcgagtag tatttttatac tttagtgaac  3596 gtggactcca gactctctgt gaaccctatg agagcgcgtc tgggcccggc catgtcctta  3656
gcacaggggg gccgccggtt tgagtgaggg tttctgagct gctctgaatt agtccttgct  3716
tggctgcttg gccttgggct tcattcaagt ctatgatgct gttgcccacg tttccgggga  3776
tatatattct ctcccctccg ttgggcccca gccttctttg cttgcctctc tgtttgtaac  3836
cttgtcgaca aagaggtaga aaagattggg tctaggatat ggtgggtgga caggggcccc  3896
gggacttgga gggttggtcc tcttgcctcc tggaaaaaac aaaaacaaaa aactgcagtg  3956
aaagacaagc tgcaaatcag ccatgtgctg cgtgcctgtg aatctggag tgaggggtaa   4016 aagctgatct ggtttgactc cgctggaggt ggggcctgga gcaggccttg cgctgttgcg  4076
taactggctg tgttctggtg aggccttgct cccaacccca cacgctcctc cctctgaggc  4136
tgtaggactc gcagtcaggg gcagctgacc atggaagatt gagagcccaa ggtttaaact  4196
tctctgaagg gaggtgggga tgagaagagg ggttttttttg tactttgtac aaagaccaca  4256
catttgtgta aacagtgttt tggaataaaa tatttttttc at                    4298

<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
agagtgcgcc gagtctgtct                                              20

<210> SEQ ID NO 6
<211> LENGTH: 20
<212> TYPE: DNA
<213> ORGANISM: Artificial Sequence
<220> FEATURE:
<223> OTHER INFORMATION: PCR Primer
```

```
<400> SEQUENCE: 6
gcattgagtg cctgcagtga                                                    20

<210> SEQ ID NO 7
<211> LENGTH: 24
<212> TYPE: DNA
<213> ORGANISM: Artificial Sequence
<220> FEATURE:
<223> OTHER INFORMATION: PCR Probe

<400> SEQUENCE: 7
tgtcatggta gagaccgagc ctct                                               24

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc                                                     19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc                                                    20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                                    20

<210> SEQ ID NO 11
<220> FEATURE:

<400> SEQUENCE: 11

000

<210> SEQ ID NO 12
<211> LENGTH: 20
<212> TYPE: DNA
<213> ORGANISM: Artificial Sequence
<220> FEATURE:
<223> OTHER INFORMATION: Antisense Compound

<400> SEQUENCE: 12
gcttggatcc tcaggctctc                                                    20

<210> SEQ ID NO 13
<211> LENGTH: 20
<212> TYPE: DNA
<213> ORGANISM: Artificial Sequence
<220> FEATURE:
```

<223> OTHER INFORMATION: Antisense Compound

<400> SEQUENCE: 13
gcttctgctg gagggccgtc                                            20

<210> SEQ ID NO 14
<211> LENGTH: 20
<212> TYPE: DNA
<213> ORGANISM: Artificial Sequence
<220> FEATURE:
<223> OTHER INFORMATION: Antisense Compound

<400> SEQUENCE: 14
tgatggtctg ctgcttccgc                                            20

<210> SEQ ID NO 15
<211> LENGTH: 20
<212> TYPE: DNA
<213> ORGANISM: Artificial Sequence
<220> FEATURE:
<223> OTHER INFORMATION: Antisense Compound

<400> SEQUENCE: 15
gcatctcctc cactgggccg                                            20

<210> SEQ ID NO 16
<211> LENGTH: 20
<212> TYPE: DNA
<213> ORGANISM: Artificial Sequence
<220> FEATURE:
<223> OTHER INFORMATION: Antisense Compound

<400> SEQUENCE: 16
cggtggctgc aaacttggtc                                            20

<210> SEQ ID NO 17
<211> LENGTH: 20
<212> TYPE: DNA
<213> ORGANISM: Artificial Sequence
<220> FEATURE:
<223> OTHER INFORMATION: Antisense Compound

<400> SEQUENCE: 17
gcacggcaaa tggcaccctg                                            20

<210> SEQ ID NO 18
<211> LENGTH: 20
<212> TYPE: DNA
<213> ORGANISM: Artificial Sequence
<220> FEATURE:
<223> OTHER INFORMATION: Antisense Compound

<400> SEQUENCE: 18
gggcctggtc catgtacgtg                                            20

<210> SEQ ID NO 19
<211> LENGTH: 20
<212> TYPE: DNA
<213> ORGANISM: Artificial Sequence
<220> FEATURE:
<223> OTHER INFORMATION: Antisense Compound

<400> SEQUENCE: 19
gagcagctca gaaaccctca                                            20

```
<210> SEQ ID NO 20
<211> LENGTH: 20
<212> TYPE: DNA
<213> ORGANISM: Artificial Sequence
<220> FEATURE:
<223> OTHER INFORMATION: Antisense Compound

<400> SEQUENCE: 20
accaaccctc caagtcccgg                                               20

<210> SEQ ID NO 21
<211> LENGTH: 20
<212> TYPE: DNA
<213> ORGANISM: Artificial Sequence
<220> FEATURE:
<223> OTHER INFORMATION: Antisense Compound

<400> SEQUENCE: 21
ccctccagga gctgggtggc                                               20

<210> SEQ ID NO 22
<211> LENGTH: 20
<212> TYPE: DNA
<213> ORGANISM: Artificial Sequence
<220> FEATURE:
<223> OTHER INFORMATION: Antisense Compound

<400> SEQUENCE: 22
ctgcaccagg ccctccagga                                               20

<210> SEQ ID NO 23
<211> LENGTH: 20
<212> TYPE: DNA
<213> ORGANISM: Artificial Sequence
<220> FEATURE:
<223> OTHER INFORMATION: Antisense Compound

<400> SEQUENCE: 23
tgcagctcct gcaccaggcc                                               20

<210> SEQ ID NO 24
<211> LENGTH: 20
<212> TYPE: DNA
<213> ORGANISM: Artificial Sequence
<220> FEATURE:
<223> OTHER INFORMATION: Antisense Compound

<400> SEQUENCE: 24
gccttcttct gcagctcctg                                               20

<210> SEQ ID NO 25
<211> LENGTH: 20
<212> TYPE: DNA
<213> ORGANISM: Artificial Sequence
<220> FEATURE:
<223> OTHER INFORMATION: Antisense Compound

<400> SEQUENCE: 25
atcttccccc acctggtgct                                               20

<210> SEQ ID NO 26
<211> LENGTH: 20
<212> TYPE: DNA
<213> ORGANISM: Artificial Sequence
<220> FEATURE:
<223> OTHER INFORMATION: Antisense Compound
```

-continued

```
<400> SEQUENCE: 26
gtaaaaaccc atcttccccc                                                20

<210> SEQ ID NO 27
<211> LENGTH: 20
<212> TYPE: DNA
<213> ORGANISM: Artificial Sequence
<220> FEATURE:
<223> OTHER INFORMATION: Antisense Compound

<400> SEQUENCE: 27
cttcagtaaa aacccatctt                                                20

<210> SEQ ID NO 28
<211> LENGTH: 20
<212> TYPE: DNA
<213> ORGANISM: Artificial Sequence
<220> FEATURE:
<223> OTHER INFORMATION: Antisense Compound

<400> SEQUENCE: 28
ccagcttgat cttcagtaaa                                                20

<210> SEQ ID NO 29
<211> LENGTH: 20
<212> TYPE: DNA
<213> ORGANISM: Artificial Sequence
<220> FEATURE:
<223> OTHER INFORMATION: Antisense Compound

<400> SEQUENCE: 29
tagtgcccca gcttgatctt                                                20

<210> SEQ ID NO 30
<211> LENGTH: 20
<212> TYPE: DNA
<213> ORGANISM: Artificial Sequence
<220> FEATURE:
<223> OTHER INFORMATION: Antisense Compound

<400> SEQUENCE: 30
cggatgcagc ggaccagctc                                                20

<210> SEQ ID NO 31
<211> LENGTH: 20
<212> TYPE: DNA
<213> ORGANISM: Artificial Sequence
<220> FEATURE:
<223> OTHER INFORMATION: Antisense Compound

<400> SEQUENCE: 31
attgttggct tctcggacca                                                20

<210> SEQ ID NO 32
<211> LENGTH: 20
<212> TYPE: DNA
<213> ORGANISM: Artificial Sequence
<220> FEATURE:
<223> OTHER INFORMATION: Antisense Compound

<400> SEQUENCE: 32
accagtcgca gctcctcaaa                                                20

<210> SEQ ID NO 33
<211> LENGTH: 20
```

```
<212> TYPE: DNA
<213> ORGANISM: Artificial Sequence
<220> FEATURE:
<223> OTHER INFORMATION: Antisense Compound

<400> SEQUENCE: 33
tcctgcgtga ccagtcgcag                                                 20

<210> SEQ ID NO 34
<211> LENGTH: 20
<212> TYPE: DNA
<213> ORGANISM: Artificial Sequence
<220> FEATURE:
<223> OTHER INFORMATION: Antisense Compound

<400> SEQUENCE: 34
tctctgtgtc ctgcgtgacc                                                 20

<210> SEQ ID NO 35
<211> LENGTH: 20
<212> TYPE: DNA
<213> ORGANISM: Artificial Sequence
<220> FEATURE:
<223> OTHER INFORMATION: Antisense Compound

<400> SEQUENCE: 35
ctcattctct gtgtcctgcg                                                 20

<210> SEQ ID NO 36
<211> LENGTH: 20
<212> TYPE: DNA
<213> ORGANISM: Artificial Sequence
<220> FEATURE:
<223> OTHER INFORMATION: Antisense Compound

<400> SEQUENCE: 36
tactcctgag tctgctgcag                                                 20

<210> SEQ ID NO 37
<211> LENGTH: 20
<212> TYPE: DNA
<213> ORGANISM: Artificial Sequence
<220> FEATURE:
<223> OTHER INFORMATION: Antisense Compound

<400> SEQUENCE: 37
tactggatga tgaagtactc                                                 20

<210> SEQ ID NO 38
<211> LENGTH: 20
<212> TYPE: DNA
<213> ORGANISM: Artificial Sequence
<220> FEATURE:
<223> OTHER INFORMATION: Antisense Compound

<400> SEQUENCE: 38
ctcaggctct cctggtactg                                                 20

<210> SEQ ID NO 39
<211> LENGTH: 20
<212> TYPE: DNA
<213> ORGANISM: Artificial Sequence
<220> FEATURE:
<223> OTHER INFORMATION: Antisense Compound

<400> SEQUENCE: 39
```

-continued caaactgagc ttggatcctc                                              20

<210> SEQ ID NO 40
<211> LENGTH: 20
<212> TYPE: DNA
<213> ORGANISM: Artificial Sequence
<220> FEATURE:
<223> OTHER INFORMATION: Antisense Compound

<400> SEQUENCE: 40
ggccgtctcc cggctcagac                                              20

<210> SEQ ID NO 41
<211> LENGTH: 20
<212> TYPE: DNA
<213> ORGANISM: Artificial Sequence
<220> FEATURE:
<223> OTHER INFORMATION: Antisense Compound

<400> SEQUENCE: 41
tggagggccg tctcccggct                                              20

<210> SEQ ID NO 42
<211> LENGTH: 20
<212> TYPE: DNA
<213> ORGANISM: Artificial Sequence
<220> FEATURE:
<223> OTHER INFORMATION: Antisense Compound

<400> SEQUENCE: 42
ccagagacac ctgcttctgc                                              20

<210> SEQ ID NO 43
<211> LENGTH: 20
<212> TYPE: DNA
<213> ORGANISM: Artificial Sequence
<220> FEATURE:
<223> OTHER INFORMATION: Antisense Compound

<400> SEQUENCE: 43
aaccaggcct ccagagacac                                              20

<210> SEQ ID NO 44
<211> LENGTH: 20
<212> TYPE: DNA
<213> ORGANISM: Artificial Sequence
<220> FEATURE:
<223> OTHER INFORMATION: Antisense Compound

<400> SEQUENCE: 44
gctgcaacca ggcctccaga                                              20

<210> SEQ ID NO 45
<211> LENGTH: 20
<212> TYPE: DNA
<213> ORGANISM: Artificial Sequence
<220> FEATURE:
<223> OTHER INFORMATION: Antisense Compound

<400> SEQUENCE: 45
tgtgcctcac gctgcaacca                                              20

<210> SEQ ID NO 46
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 46
ctgcagtgtc tgtgcctcac                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Compound

<400> SEQUENCE: 47
cgcggtactg ctgcagtgtc                                               20

<210> SEQ ID NO 48
<211> LENGTH: 20
<212> TYPE: DNA
<213> ORGANISM: Artificial Sequence
<220> FEATURE:
<223> OTHER INFORMATION: Antisense Compound

<400> SEQUENCE: 48
gcttctcggc cagctccacg                                               20

<210> SEQ ID NO 49
<211> LENGTH: 20
<212> TYPE: DNA
<213> ORGANISM: Artificial Sequence
<220> FEATURE:
<223> OTHER INFORMATION: Antisense Compound

<400> SEQUENCE: 49
ctggtgcttc tcggccagct                                               20

<210> SEQ ID NO 50
<211> LENGTH: 20
<212> TYPE: DNA
<213> ORGANISM: Artificial Sequence
<220> FEATURE:
<223> OTHER INFORMATION: Antisense Compound

<400> SEQUENCE: 50
agggtcttct ggtgcttctc                                               20

<210> SEQ ID NO 51
<211> LENGTH: 20
<212> TYPE: DNA
<213> ORGANISM: Artificial Sequence
<220> FEATURE:
<223> OTHER INFORMATION: Antisense Compound

<400> SEQUENCE: 51
gctgcagggt cttctggtgc                                               20

<210> SEQ ID NO 52
<211> LENGTH: 20
<212> TYPE: DNA
<213> ORGANISM: Artificial Sequence
<220> FEATURE:
<223> OTHER INFORMATION: Antisense Compound

<400> SEQUENCE: 52
ttccgcagca gctgcagggt                                               20
```

<210> SEQ ID NO 53
<211> LENGTH: 20
<212> TYPE: DNA
<213> ORGANISM: Artificial Sequence
<220> FEATURE:
<223> OTHER INFORMATION: Antisense Compound

<400> SEQUENCE: 53
ccaggatgat ggtctgctgc 20

<210> SEQ ID NO 54
<211> LENGTH: 20
<212> TYPE: DNA
<213> ORGANISM: Artificial Sequence
<220> FEATURE:
<223> OTHER INFORMATION: Antisense Compound

<400> SEQUENCE: 54
cgtcatccag gatgatggtc 20

<210> SEQ ID NO 55
<211> LENGTH: 20
<212> TYPE: DNA
<213> ORGANISM: Artificial Sequence
<220> FEATURE:
<223> OTHER INFORMATION: Antisense Compound

<400> SEQUENCE: 55
gcttccactg gatcagctcg 20

<210> SEQ ID NO 56
<211> LENGTH: 20
<212> TYPE: DNA
<213> ORGANISM: Artificial Sequence
<220> FEATURE:
<223> OTHER INFORMATION: Antisense Compound

<400> SEQUENCE: 56
tgctgccgcc gcttccactg 20

<210> SEQ ID NO 57
<211> LENGTH: 20
<212> TYPE: DNA
<213> ORGANISM: Artificial Sequence
<220> FEATURE:
<223> OTHER INFORMATION: Antisense Compound

<400> SEQUENCE: 57
acgtccaggc tgccctcggg 20

<210> SEQ ID NO 58
<211> LENGTH: 20
<212> TYPE: DNA
<213> ORGANISM: Artificial Sequence
<220> FEATURE:
<223> OTHER INFORMATION: Antisense Compound

<400> SEQUENCE: 58
caggactgta gcacgtccag 20

<210> SEQ ID NO 59
<211> LENGTH: 20
<212> TYPE: DNA
<213> ORGANISM: Artificial Sequence
<220> FEATURE:
<223> OTHER INFORMATION: Antisense Compound

<400> SEQUENCE: 59
cttctcacac caggactgta                                                                                   20

<210> SEQ ID NO 60
<211> LENGTH: 20
<212> TYPE: DNA
<213> ORGANISM: Artificial Sequence
<220> FEATURE:
<223> OTHER INFORMATION: Antisense Compound

<400> SEQUENCE: 60
tctcggccaa cttctcacac                                                                                   20

<210> SEQ ID NO 61
<211> LENGTH: 20
<212> TYPE: DNA
<213> ORGANISM: Artificial Sequence
<220> FEATURE:
<223> OTHER INFORMATION: Antisense Compound

<400> SEQUENCE: 61
tgccagatga tctcggccaa                                                                                   20

<210> SEQ ID NO 62
<211> LENGTH: 20
<212> TYPE: DNA
<213> ORGANISM: Artificial Sequence
<220> FEATURE:
<223> OTHER INFORMATION: Antisense Compound

<400> SEQUENCE: 62
ctgccggttc tgccagatga                                                                                   20

<210> SEQ ID NO 63
<211> LENGTH: 20
<212> TYPE: DNA
<213> ORGANISM: Artificial Sequence
<220> FEATURE:
<223> OTHER INFORMATION: Antisense Compound

<400> SEQUENCE: 63
tgcggatctg ctgccggttc                                                                                   20

<210> SEQ ID NO 64
<211> LENGTH: 20
<212> TYPE: DNA
<213> ORGANISM: Artificial Sequence
<220> FEATURE:
<223> OTHER INFORMATION: Antisense Compound

<400> SEQUENCE: 64
tgctcagccc tgcggatctg                                                                                   20

<210> SEQ ID NO 65
<211> LENGTH: 20
<212> TYPE: DNA
<213> ORGANISM: Artificial Sequence
<220> FEATURE:
<223> OTHER INFORMATION: Antisense Compound

<400> SEQUENCE: 65
ctggcagagg tgctcagccc                                                                                   20

<210> SEQ ID NO 66

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 66
atgggcagct gctggcagag                                                   20

<210> SEQ ID NO 67
<211> LENGTH: 20
<212> TYPE: DNA
<213> ORGANISM: Artificial Sequence
<220> FEATURE:
<223> OTHER INFORMATION: Antisense Compound

<400> SEQUENCE: 67
gacctcggcc agcatctcct                                                   20

<210> SEQ ID NO 68
<211> LENGTH: 20
<212> TYPE: DNA
<213> ORGANISM: Artificial Sequence
<220> FEATURE:
<223> OTHER INFORMATION: Antisense Compound

<400> SEQUENCE: 68
aatgtccgtg atggtggcgt                                                   20

<210> SEQ ID NO 69
<211> LENGTH: 20
<212> TYPE: DNA
<213> ORGANISM: Artificial Sequence
<220> FEATURE:
<223> OTHER INFORMATION: Antisense Compound

<400> SEQUENCE: 69
ggctgagata atgtccgtga                                                   20

<210> SEQ ID NO 70
<211> LENGTH: 20
<212> TYPE: DNA
<213> ORGANISM: Artificial Sequence
<220> FEATURE:
<223> OTHER INFORMATION: Antisense Compound

<400> SEQUENCE: 70
tggtcaccag ggctgagata                                                   20

<210> SEQ ID NO 71
<211> LENGTH: 20
<212> TYPE: DNA
<213> ORGANISM: Artificial Sequence
<220> FEATURE:
<223> OTHER INFORMATION: Antisense Compound

<400> SEQUENCE: 71
ggctgcttct caatgatgaa                                                   20

<210> SEQ ID NO 72
<211> LENGTH: 20
<212> TYPE: DNA
<213> ORGANISM: Artificial Sequence
<220> FEATURE:
<223> OTHER INFORMATION: Antisense Compound

<400> SEQUENCE: 72
```
ggtcttcagg acctgaggag                                                  20

<210> SEQ ID NO 73
<211> LENGTH: 20
<212> TYPE: DNA
<213> ORGANISM: Artificial Sequence
<220> FEATURE:
<223> OTHER INFORMATION: Antisense Compound

<400> SEQUENCE: 73
gatggtggcc ttcacctggg                                                  20

<210> SEQ ID NO 74
<211> LENGTH: 20
<212> TYPE: DNA
<213> ORGANISM: Artificial Sequence
<220> FEATURE:
<223> OTHER INFORMATION: Antisense Compound

<400> SEQUENCE: 74
gctcactgat gatggtggcc                                                  20

<210> SEQ ID NO 75
<211> LENGTH: 20
<212> TYPE: DNA
<213> ORGANISM: Artificial Sequence
<220> FEATURE:
<223> OTHER INFORMATION: Antisense Compound

<400> SEQUENCE: 75
ttggcctgct gctcactgat                                                  20

<210> SEQ ID NO 76
<211> LENGTH: 20
<212> TYPE: DNA
<213> ORGANISM: Artificial Sequence
<220> FEATURE:
<223> OTHER INFORMATION: Antisense Compound

<400> SEQUENCE: 76
agcagagact tggcctgctg                                                  20

<210> SEQ ID NO 77
<211> LENGTH: 20
<212> TYPE: DNA
<213> ORGANISM: Artificial Sequence
<220> FEATURE:
<223> OTHER INFORMATION: Antisense Compound

<400> SEQUENCE: 77
gtggcttggt ggtactccat                                                  20

<210> SEQ ID NO 78
<211> LENGTH: 20
<212> TYPE: DNA
<213> ORGANISM: Artificial Sequence
<220> FEATURE:
<223> OTHER INFORMATION: Antisense Compound

<400> SEQUENCE: 78
gccacagcac tttgtcaggc                                                  20

<210> SEQ ID NO 79
<211> LENGTH: 20
<212> TYPE: DNA

```
<213> ORGANISM: Artificial Sequence
<220> FEATURE:
<223> OTHER INFORMATION: Antisense Compound

<400> SEQUENCE: 79
ttgaatttca tgttgagcgc                                                      20

<210> SEQ ID NO 80
<211> LENGTH: 20
<212> TYPE: DNA
<213> ORGANISM: Artificial Sequence
<220> FEATURE:
<223> OTHER INFORMATION: Antisense Compound

<400> SEQUENCE: 80
ggttgctctg cacttcggcc                                                      20

<210> SEQ ID NO 81
<211> LENGTH: 20
<212> TYPE: DNA
<213> ORGANISM: Artificial Sequence
<220> FEATURE:
<223> OTHER INFORMATION: Antisense Compound

<400> SEQUENCE: 81
gttctccttg gtcaggcccc                                                      20

<210> SEQ ID NO 82
<211> LENGTH: 20
<212> TYPE: DNA
<213> ORGANISM: Artificial Sequence
<220> FEATURE:
<223> OTHER INFORMATION: Antisense Compound

<400> SEQUENCE: 82
ttctgcgcca ggaacacgag                                                      20

<210> SEQ ID NO 83
<211> LENGTH: 20
<212> TYPE: DNA
<213> ORGANISM: Artificial Sequence
<220> FEATURE:
<223> OTHER INFORMATION: Antisense Compound

<400> SEQUENCE: 83
tgctgctgtt gttgaacagt                                                      20

<210> SEQ ID NO 84
<211> LENGTH: 20
<212> TYPE: DNA
<213> ORGANISM: Artificial Sequence
<220> FEATURE:
<223> OTHER INFORMATION: Antisense Compound

<400> SEQUENCE: 84
actgtagtcc tccaggtggc                                                      20

<210> SEQ ID NO 85
<211> LENGTH: 20
<212> TYPE: DNA
<213> ORGANISM: Artificial Sequence
<220> FEATURE:
<223> OTHER INFORMATION: Antisense Compound

<400> SEQUENCE: 85
gacaggccac tgtagtcctc                                                      20
```

<210> SEQ ID NO 86
<211> LENGTH: 20
<212> TYPE: DNA
<213> ORGANISM: Artificial Sequence
<220> FEATURE:
<223> OTHER INFORMATION: Antisense Compound

<400> SEQUENCE: 86
tatccatcaa cagctttagc                                             20

<210> SEQ ID NO 87
<211> LENGTH: 20
<212> TYPE: DNA
<213> ORGANISM: Artificial Sequence
<220> FEATURE:
<223> OTHER INFORMATION: Antisense Compound

<400> SEQUENCE: 87
accacttgct tgatctgtgg                                             20

<210> SEQ ID NO 88
<211> LENGTH: 20
<212> TYPE: DNA
<213> ORGANISM: Artificial Sequence
<220> FEATURE:
<223> OTHER INFORMATION: Antisense Compound

<400> SEQUENCE: 88
aaactcaggg accacttgct                                             20

<210> SEQ ID NO 89
<211> LENGTH: 20
<212> TYPE: DNA
<213> ORGANISM: Artificial Sequence
<220> FEATURE:
<223> OTHER INFORMATION: Antisense Compound

<400> SEQUENCE: 89
tctgtgggta catgttatag                                             20

<210> SEQ ID NO 90
<211> LENGTH: 20
<212> TYPE: DNA
<213> ORGANISM: H. sapiens
<220> FEATURE:

<400> SEQUENCE: 90
gcggaagcag cagaccatca                                             20

<210> SEQ ID NO 91
<211> LENGTH: 20
<212> TYPE: DNA
<213> ORGANISM: H. sapiens
<220> FEATURE:

<400> SEQUENCE: 91
cggcccagtg gaggagatgc                                             20

<210> SEQ ID NO 92
<211> LENGTH: 20
<212> TYPE: DNA
<213> ORGANISM: H. sapiens
<220> FEATURE:

<400> SEQUENCE: 92

-continued gaccaagttt gcagccaccg                    20

<210> SEQ ID NO 93
<211> LENGTH: 20
<212> TYPE: DNA
<213> ORGANISM: H. sapiens
<220> FEATURE:

<400> SEQUENCE: 93
tgagggtttc tgagctgctc                    20

<210> SEQ ID NO 94
<211> LENGTH: 20
<212> TYPE: DNA
<213> ORGANISM: H. sapiens
<220> FEATURE:

<400> SEQUENCE: 94
ccgggacttg gagggttggt                    20

<210> SEQ ID NO 95
<211> LENGTH: 20
<212> TYPE: DNA
<213> ORGANISM: H. sapiens
<220> FEATURE:

<400> SEQUENCE: 95
gccacccagc tcctggaggg                    20

<210> SEQ ID NO 96
<211> LENGTH: 20
<212> TYPE: DNA
<213> ORGANISM: H. sapiens
<220> FEATURE:

<400> SEQUENCE: 96
tcctggaggg cctggtgcag                    20

<210> SEQ ID NO 97
<211> LENGTH: 20
<212> TYPE: DNA
<213> ORGANISM: H. sapiens
<220> FEATURE:

<400> SEQUENCE: 97
ggcctggtgc aggagctgca                    20

<210> SEQ ID NO 98
<211> LENGTH: 20
<212> TYPE: DNA
<213> ORGANISM: H. sapiens
<220> FEATURE:

<400> SEQUENCE: 98
caggagctgc agaagaaggc                    20

<210> SEQ ID NO 99
<211> LENGTH: 20
<212> TYPE: DNA
<213> ORGANISM: H. sapiens
<220> FEATURE:

<400> SEQUENCE: 99
agcaccaggt gggggaagat                    20

```
<210> SEQ ID NO 100
<211> LENGTH: 20
<212> TYPE: DNA
<213> ORGANISM: H. sapiens
<220> FEATURE:

<400> SEQUENCE: 100
tttactgaag atcaagctgg                                               20

<210> SEQ ID NO 101
<211> LENGTH: 20
<212> TYPE: DNA
<213> ORGANISM: H. sapiens
<220> FEATURE:

<400> SEQUENCE: 101
aagatcaagc tggggcacta                                               20

<210> SEQ ID NO 102
<211> LENGTH: 20
<212> TYPE: DNA
<213> ORGANISM: H. sapiens
<220> FEATURE:

<400> SEQUENCE: 102
gagctggtcc gctgcatccg                                               20

<210> SEQ ID NO 103
<211> LENGTH: 20
<212> TYPE: DNA
<213> ORGANISM: H. sapiens
<220> FEATURE:

<400> SEQUENCE: 103
tggtccgaga agccaacaat                                               20

<210> SEQ ID NO 104
<211> LENGTH: 20
<212> TYPE: DNA
<213> ORGANISM: H. sapiens
<220> FEATURE:

<400> SEQUENCE: 104
tttgaggagc tgcgactggt                                               20

<210> SEQ ID NO 105
<211> LENGTH: 20
<212> TYPE: DNA
<213> ORGANISM: H. sapiens
<220> FEATURE:

<400> SEQUENCE: 105
ctgcgactgg tcacgcagga                                               20

<210> SEQ ID NO 106
<211> LENGTH: 20
<212> TYPE: DNA
<213> ORGANISM: H. sapiens
<220> FEATURE:

<400> SEQUENCE: 106
ggtcacgcag gacacagaga                                               20
```

```
<210> SEQ ID NO 107
<211> LENGTH: 20
<212> TYPE: DNA
<213> ORGANISM: H. sapiens
<220> FEATURE:

<400> SEQUENCE: 107
cgcaggacac agagaatgag                                              20

<210> SEQ ID NO 108
<211> LENGTH: 20
<212> TYPE: DNA
<213> ORGANISM: H. sapiens
<220> FEATURE:

<400> SEQUENCE: 108
ctgcagcaga ctcaggagta                                              20

<210> SEQ ID NO 109
<211> LENGTH: 20
<212> TYPE: DNA
<213> ORGANISM: H. sapiens
<220> FEATURE:

<400> SEQUENCE: 109
gagtacttca tcatccagta                                              20

<210> SEQ ID NO 110
<211> LENGTH: 20
<212> TYPE: DNA
<213> ORGANISM: H. sapiens
<220> FEATURE:

<400> SEQUENCE: 110
cagtaccagg agagcctgag                                              20

<210> SEQ ID NO 111
<211> LENGTH: 20
<212> TYPE: DNA
<213> ORGANISM: H. sapiens
<220> FEATURE:

<400> SEQUENCE: 111
gaggatccaa gctcagtttg                                              20

<210> SEQ ID NO 112
<211> LENGTH: 20
<212> TYPE: DNA
<213> ORGANISM: H. sapiens
<220> FEATURE:

<400> SEQUENCE: 112
agccgggaga cggccctcca                                              20

<210> SEQ ID NO 113
<211> LENGTH: 20
<212> TYPE: DNA
<213> ORGANISM: H. sapiens
<220> FEATURE:

<400> SEQUENCE: 113
gcagaagcag gtgtctctgg                                              20

<210> SEQ ID NO 114
<211> LENGTH: 20
```

```
<212> TYPE: DNA
<213> ORGANISM: H. sapiens
<220> FEATURE:

<400> SEQUENCE: 114
gtgtctctgg aggcctggtt                                           20

<210> SEQ ID NO 115
<211> LENGTH: 20
<212> TYPE: DNA
<213> ORGANISM: H. sapiens
<220> FEATURE:

<400> SEQUENCE: 115
tctggaggcc tggttgcagc                                           20

<210> SEQ ID NO 116
<211> LENGTH: 20
<212> TYPE: DNA
<213> ORGANISM: H. sapiens
<220> FEATURE:

<400> SEQUENCE: 116
tggttgcagc gtgaggcaca                                           20

<210> SEQ ID NO 117
<211> LENGTH: 20
<212> TYPE: DNA
<213> ORGANISM: H. sapiens
<220> FEATURE:

<400> SEQUENCE: 117
gtgaggcaca gacactgcag                                           20

<210> SEQ ID NO 118
<211> LENGTH: 20
<212> TYPE: DNA
<213> ORGANISM: H. sapiens
<220> FEATURE:

<400> SEQUENCE: 118
gacactgcag cagtaccgcg                                           20

<210> SEQ ID NO 119
<211> LENGTH: 20
<212> TYPE: DNA
<213> ORGANISM: H. sapiens
<220> FEATURE:

<400> SEQUENCE: 119
cgtggagctg gccgagaagc                                           20

<210> SEQ ID NO 120
<211> LENGTH: 20
<212> TYPE: DNA
<213> ORGANISM: H. sapiens
<220> FEATURE:

<400> SEQUENCE: 120
agctggccga gaagcaccag                                           20

<210> SEQ ID NO 121
<211> LENGTH: 20
<212> TYPE: DNA
<213> ORGANISM: H. sapiens
```

```
<220> FEATURE:

<400> SEQUENCE: 121
gcagcagacc atcatcctgg                                                   20

<210> SEQ ID NO 122
<211> LENGTH: 20
<212> TYPE: DNA
<213> ORGANISM: H. sapiens
<220> FEATURE:

<400> SEQUENCE: 122
gaccatcatc ctggatgacg                                                   20

<210> SEQ ID NO 123
<211> LENGTH: 20
<212> TYPE: DNA
<213> ORGANISM: H. sapiens
<220> FEATURE:

<400> SEQUENCE: 123
cgagctgatc cagtggaagc                                                   20

<210> SEQ ID NO 124
<211> LENGTH: 20
<212> TYPE: DNA
<213> ORGANISM: H. sapiens
<220> FEATURE:

<400> SEQUENCE: 124
cagtggaagc ggcggcagca                                                   20

<210> SEQ ID NO 125
<211> LENGTH: 20
<212> TYPE: DNA
<213> ORGANISM: H. sapiens
<220> FEATURE:

<400> SEQUENCE: 125
cccgagggca gcctggacgt                                                   20

<210> SEQ ID NO 126
<211> LENGTH: 20
<212> TYPE: DNA
<213> ORGANISM: H. sapiens
<220> FEATURE:

<400> SEQUENCE: 126
ctggacgtgc tacagtcctg                                                   20

<210> SEQ ID NO 127
<211> LENGTH: 20
<212> TYPE: DNA
<213> ORGANISM: H. sapiens
<220> FEATURE:

<400> SEQUENCE: 127
tacagtcctg gtgtgagaag                                                   20

<210> SEQ ID NO 128
<211> LENGTH: 20
<212> TYPE: DNA
<213> ORGANISM: H. sapiens
<220> FEATURE:
```

```
<400> SEQUENCE: 128
gtgtgagaag ttggccgaga                                              20

<210> SEQ ID NO 129
<211> LENGTH: 20
<212> TYPE: DNA
<213> ORGANISM: H. sapiens
<220> FEATURE:

<400> SEQUENCE: 129
ttggccgaga tcatctggca                                              20

<210> SEQ ID NO 130
<211> LENGTH: 20
<212> TYPE: DNA
<213> ORGANISM: H. sapiens
<220> FEATURE:

<400> SEQUENCE: 130
tcatctggca gaaccggcag                                              20

<210> SEQ ID NO 131
<211> LENGTH: 20
<212> TYPE: DNA
<213> ORGANISM: H. sapiens
<220> FEATURE:

<400> SEQUENCE: 131
gaaccggcag cagatccgca                                              20

<210> SEQ ID NO 132
<211> LENGTH: 20
<212> TYPE: DNA
<213> ORGANISM: H. sapiens
<220> FEATURE:

<400> SEQUENCE: 132
cagatccgca gggctgagca                                              20

<210> SEQ ID NO 133
<211> LENGTH: 20
<212> TYPE: DNA
<213> ORGANISM: H. sapiens
<220> FEATURE:

<400> SEQUENCE: 133
gggctgagca cctctgccag                                              20

<210> SEQ ID NO 134
<211> LENGTH: 20
<212> TYPE: DNA
<213> ORGANISM: H. sapiens
<220> FEATURE:

<400> SEQUENCE: 134
acgccaccat cacggacatt                                              20

<210> SEQ ID NO 135
<211> LENGTH: 20
<212> TYPE: DNA
<213> ORGANISM: H. sapiens
<220> FEATURE:

<400> SEQUENCE: 135
```

| | |
|---|---|
| tcacggacat tatctcagcc | 20 |

<210> SEQ ID NO 136
<211> LENGTH: 20
<212> TYPE: DNA
<213> ORGANISM: H. sapiens
<220> FEATURE:

<400> SEQUENCE: 136

| | |
|---|---|
| tatctcagcc ctggtgacca | 20 |

<210> SEQ ID NO 137
<211> LENGTH: 20
<212> TYPE: DNA
<213> ORGANISM: H. sapiens
<220> FEATURE:

<400> SEQUENCE: 137

| | |
|---|---|
| ctcctcaggt cctgaagacc | 20 |

<210> SEQ ID NO 138
<211> LENGTH: 20
<212> TYPE: DNA
<213> ORGANISM: H. sapiens
<220> FEATURE:

<400> SEQUENCE: 138

| | |
|---|---|
| ggccaccatc atcagtgagc | 20 |

<210> SEQ ID NO 139
<211> LENGTH: 20
<212> TYPE: DNA
<213> ORGANISM: H. sapiens
<220> FEATURE:

<400> SEQUENCE: 139

| | |
|---|---|
| atcagtgagc agcaggccaa | 20 |

<210> SEQ ID NO 140
<211> LENGTH: 20
<212> TYPE: DNA
<213> ORGANISM: H. sapiens
<220> FEATURE:

<400> SEQUENCE: 140

| | |
|---|---|
| cagcaggcca agtctctgct | 20 |

<210> SEQ ID NO 141
<211> LENGTH: 20
<212> TYPE: DNA
<213> ORGANISM: H. sapiens
<220> FEATURE:

<400> SEQUENCE: 141

| | |
|---|---|
| atggagtacc accaagccac | 20 |

<210> SEQ ID NO 142
<211> LENGTH: 20
<212> TYPE: DNA
<213> ORGANISM: H. sapiens
<220> FEATURE:

<400> SEQUENCE: 142

| | |
|---|---|
| gcctgacaaa gtgctgtggc | 20 |

```
<210> SEQ ID NO 143
<211> LENGTH: 20
<212> TYPE: DNA
<213> ORGANISM: H. sapiens
<220> FEATURE:

<400> SEQUENCE: 143
gcgctcaaca tgaaattcaa                                               20

<210> SEQ ID NO 144
<211> LENGTH: 20
<212> TYPE: DNA
<213> ORGANISM: H. sapiens
<220> FEATURE:

<400> SEQUENCE: 144
ggggcctgac caaggagaac                                               20

<210> SEQ ID NO 145
<211> LENGTH: 20
<212> TYPE: DNA
<213> ORGANISM: H. sapiens
<220> FEATURE:

<400> SEQUENCE: 145
ctcgtgttcc tggcgcagaa                                               20

<210> SEQ ID NO 146
<211> LENGTH: 20
<212> TYPE: DNA
<213> ORGANISM: H. sapiens
<220> FEATURE:

<400> SEQUENCE: 146
actgttcaac aacagcagca                                               20

<210> SEQ ID NO 147
<211> LENGTH: 20
<212> TYPE: DNA
<213> ORGANISM: H. sapiens
<220> FEATURE:

<400> SEQUENCE: 147
gctaaagctg ttgatggata                                               20

<210> SEQ ID NO 148
<211> LENGTH: 20
<212> TYPE: DNA
<213> ORGANISM: H. sapiens
<220> FEATURE:

<400> SEQUENCE: 148
ccacagatca agcaagtggt                                               20

<210> SEQ ID NO 149
<211> LENGTH: 20
<212> TYPE: DNA
<213> ORGANISM: H. sapiens
<220> FEATURE:

<400> SEQUENCE: 149
agcaagtggt ccctgagttt                                               20

<210> SEQ ID NO 150
```

```
<211> LENGTH: 20
<212> TYPE: DNA
<213> ORGANISM: H. sapiens
<220> FEATURE:

<400> SEQUENCE: 150
ctataacatg tacccacaga                                              20

<210> SEQ ID NO 151
<211> LENGTH: 2716
<212> TYPE: DNA
<213> ORGANISM: H. sapiens
<220> FEATURE:
<221> NAME/KEY: CDS
<222> LOCATION: (12)...(2375)
<223> OTHER INFORMATION: Antisense compound

<400> SEQUENCE: 151
```

| | | | | | | | | | | | | | | |
|---|---|---|---|---|---|---|---|---|---|---|---|---|---|---|
| ccgggtaaac | c | atg | gct | gtg | tgg | ata | caa | gct | cag | cag | ctc | caa | gga | gaa | 50 |
| | | Met | Ala | Val | Trp | Ile | Gln | Ala | Gln | Gln | Leu | Gln | Gly | Glu | |
| | | 1 | | 5 | | | | | 10 | | | | | | |

| | | | | | | | | | | | | | |
|---|---|---|---|---|---|---|---|---|---|---|---|---|---|
| gcc | ctt | cat | cag | atg | cag | gcg | tta | tat | ggc | cag | cat | ttt | ccc att gag | 98 |
| Ala | Leu | His | Gln | Met | Gln | Ala | Leu | Tyr | Gly | Gln | His | Phe | Pro Ile Glu | |
| 15 | | | | | 20 | | | | | 25 | | | | |

| | | | | | | | | | | | | | | |
|---|---|---|---|---|---|---|---|---|---|---|---|---|---|---|
| gtg | cgg | cat | tat | tta | tcc | cag | tgg | att | gaa | agc | caa | gca | tgg gac tca | 146 |
| Val | Arg | His | Tyr | Leu | Ser | Gln | Trp | Ile | Glu | Ser | Gln | Ala | Trp Asp Ser | |
| 30 | | | | | 35 | | | | | 40 | | | | 45 |

| | | | | | | | | | | | | | | |
|---|---|---|---|---|---|---|---|---|---|---|---|---|---|---|
| gta | gat | ctt | gat | aat | cca | cag | gag | aac | att | aag | gcc | acc | cag ctc ctg | 194 |
| Val | Asp | Leu | Asp | Asn | Pro | Gln | Glu | Asn | Ile | Lys | Ala | Thr | Gln Leu Leu | |
| | | | | 50 | | | | | 55 | | | | | 60 |

| | | | | | | | | | | | | | | |
|---|---|---|---|---|---|---|---|---|---|---|---|---|---|---|
| gag | ggc | ctg | gtg | cag | gag | ctg | cag | aag | aag | gca | gag | cac | cag gtg ggg | 242 |
| Glu | Gly | Leu | Val | Gln | Glu | Leu | Gln | Lys | Lys | Ala | Glu | His | Gln Val Gly | |
| | | 65 | | | | | 70 | | | | | 75 | | |

| | | | | | | | | | | | | | | |
|---|---|---|---|---|---|---|---|---|---|---|---|---|---|---|
| gaa | gat | ggg | ttt | tta | ctg | aag | atc | aag | ctg | ggg | cac | tat | gcc aca cag | 290 |
| Glu | Asp | Gly | Phe | Leu | Leu | Lys | Ile | Lys | Leu | Gly | His | Tyr | Ala Thr Gln | |
| | | 80 | | | | | 85 | | | | | 90 | | |

| | | | | | | | | | | | | | | |
|---|---|---|---|---|---|---|---|---|---|---|---|---|---|---|
| ctc | cag | aac | acg | tat | gac | cgc | tgc | ccc | atg | gag | ctg | gtc | cgc tgc atc | 338 |
| Leu | Gln | Asn | Thr | Tyr | Asp | Arg | Cys | Pro | Met | Glu | Leu | Val | Arg Cys Ile | |
| | 95 | | | | | 100 | | | | | 105 | | | |

| | | | | | | | | | | | | | | |
|---|---|---|---|---|---|---|---|---|---|---|---|---|---|---|
| cgc | cat | ata | ttg | tac | aat | gaa | cag | agg | ttg | gtc | cga | gaa | gcc aac aat | 386 |
| Arg | His | Ile | Leu | Tyr | Asn | Glu | Gln | Arg | Leu | Val | Arg | Glu | Ala Asn Asn | |
| 110 | | | | | 115 | | | | | 120 | | | | 125 |

| | | | | | | | | | | | | | | |
|---|---|---|---|---|---|---|---|---|---|---|---|---|---|---|
| ggt | agc | tct | cca | gct | gga | agc | ctt | gct | gat | gcc | atg | tcc | cag aaa cac | 434 |
| Gly | Ser | Ser | Pro | Ala | Gly | Ser | Leu | Ala | Asp | Ala | Met | Ser | Gln Lys His | |
| | | | | 130 | | | | | 135 | | | | | 140 |

| | | | | | | | | | | | | | | |
|---|---|---|---|---|---|---|---|---|---|---|---|---|---|---|
| ctc | cag | atc | aac | cag | acg | ttt | gag | gag | ctg | cga | ctg | gtc | acg cag gac | 482 |
| Leu | Gln | Ile | Asn | Gln | Thr | Phe | Glu | Glu | Leu | Arg | Leu | Val | Thr Gln Asp | |
| | | | | 145 | | | | | 150 | | | | | 155 |

| | | | | | | | | | | | | | | |
|---|---|---|---|---|---|---|---|---|---|---|---|---|---|---|
| aca | gag | aat | gag | tta | aaa | aag | ctg | cag | cag | act | cag | gag | tac ttc atc | 530 |
| Thr | Glu | Asn | Glu | Leu | Lys | Lys | Leu | Gln | Gln | Thr | Gln | Glu | Tyr Phe Ile | |
| | | | | 160 | | | | | 165 | | | | | 170 |

| | | | | | | | | | | | | | | |
|---|---|---|---|---|---|---|---|---|---|---|---|---|---|---|
| atc | cag | tac | cag | gag | agc | ctg | agg | atc | caa | gct | cag | ttt | ggc ccg ctg | 578 |
| Ile | Gln | Tyr | Gln | Glu | Ser | Leu | Arg | Ile | Gln | Ala | Gln | Phe | Gly Pro Leu | |
| | 175 | | | | | 180 | | | | | 185 | | | |

| | | | | | | | | | | | | | | |
|---|---|---|---|---|---|---|---|---|---|---|---|---|---|---|
| gcc | cag | ctg | agc | ccc | cag | gag | cgt | ctg | agc | cgg | gag | acg | gcc ctc cag | 626 |
| Ala | Gln | Leu | Ser | Pro | Gln | Glu | Arg | Leu | Ser | Arg | Glu | Thr | Ala Leu Gln | |
| 190 | | | | | 195 | | | | | 200 | | | | 205 |

| | | | | | | | | | | | | | | |
|---|---|---|---|---|---|---|---|---|---|---|---|---|---|---|
| cag | aag | cag | gtg | tct | ctg | gag | gcc | tgg | ttg | cag | cgt | gag | gca cag aca | 674 |
| Gln | Lys | Gln | Val | Ser | Leu | Glu | Ala | Trp | Leu | Gln | Arg | Glu | Ala Gln Thr | |
| | | | | 210 | | | | | 215 | | | | | 220 |

| | | | | | | | | | | | | | | |
|---|---|---|---|---|---|---|---|---|---|---|---|---|---|---|
| ctg | cag | cag | tac | cgc | gtg | gag | ctg | gcc | gag | aag | cac | cag | aag acc ctg | 722 |
| Leu | Gln | Gln | Tyr | Arg | Val | Glu | Leu | Ala | Glu | Lys | His | Gln | Lys Thr Leu | |

-continued

|  |  |  |  |  |
|---|---|---|---|---|
| | 225 | 230 | 235 | |
| cag ctg ctg cgg aag cag cag acc atc atc ctg gat gac gag ctg atc<br>Gln Leu Leu Arg Lys Gln Gln Thr Ile Ile Leu Asp Asp Glu Leu Ile<br>240 245 250 | | | | 770 |
| cag tgg aag cgg cgg cag cag ctg gcc ggg aac ggc ggg ccc ccc gag<br>Gln Trp Lys Arg Arg Gln Gln Leu Ala Gly Asn Gly Gly Pro Pro Glu<br>255 260 265 | | | | 818 |
| ggc agc ctg gac gtg cta cag tcc tgg tgt gag aag ttg gcc gag atc<br>Gly Ser Leu Asp Val Leu Gln Ser Trp Cys Glu Lys Leu Ala Glu Ile<br>270 275 280 285 | | | | 866 |
| atc tgg cag aac cgg cag cag atc cgc agg gct gag cac ctc tgc cag<br>Ile Trp Gln Asn Arg Gln Gln Ile Arg Arg Ala Glu His Leu Cys Gln<br>290 295 300 | | | | 914 |
| cag ctg ccc atc ccc ggc cca gtg gag gag atg ctg gcc gag gtc aac<br>Gln Leu Pro Ile Pro Gly Pro Val Glu Glu Met Leu Ala Glu Val Asn<br>305 310 315 | | | | 962 |
| gcc acc atc acg gac att atc tca gcc ctg gtg acc agc acg ttc atc<br>Ala Thr Ile Thr Asp Ile Ile Ser Ala Leu Val Thr Ser Thr Phe Ile<br>320 325 330 | | | | 1010 |
| att gag aag cag cct cct cag gtc ctg aag acc cag acc aag ttt gca<br>Ile Glu Lys Gln Pro Pro Gln Val Leu Lys Thr Gln Thr Lys Phe Ala<br>335 340 345 | | | | 1058 |
| gcc act gtg cgc ctg ctg gtg ggc ggg aag ctg aac gtg cac atg aac<br>Ala Thr Val Arg Leu Leu Val Gly Gly Lys Leu Asn Val His Met Asn<br>350 355 360 365 | | | | 1106 |
| ccc ccc cag gtg aag gcc acc atc atc agt gag cag cag gcc aag tct<br>Pro Pro Gln Val Lys Ala Thr Ile Ile Ser Glu Gln Gln Ala Lys Ser<br>370 375 380 | | | | 1154 |
| ctg ctc aag aac gag aac acc cgc aat gat tac agt ggc gag atc ttg<br>Leu Leu Lys Asn Glu Asn Thr Arg Asn Asp Tyr Ser Gly Glu Ile Leu<br>385 390 395 | | | | 1202 |
| aac aac tgc tgc gtc atg gag tac cac caa gcc aca ggc acc ctt agt<br>Asn Asn Cys Cys Val Met Glu Tyr His Gln Ala Thr Gly Thr Leu Ser<br>400 405 410 | | | | 1250 |
| gcc cac ttc agg aat atg tcc ctg aaa cga att aag agg tca gac cgt<br>Ala His Phe Arg Asn Met Ser Leu Lys Arg Ile Lys Arg Ser Asp Arg<br>415 420 425 | | | | 1298 |
| cgt ggg gca gag tcg gtg aca gaa gaa aaa ttt aca atc ctg ttt gaa<br>Arg Gly Ala Glu Ser Val Thr Glu Glu Lys Phe Thr Ile Leu Phe Glu<br>430 435 440 445 | | | | 1346 |
| tcc cag ttc agt gtt ggt gga aat gag ctg gtt ttt caa gtc aag acc<br>Ser Gln Phe Ser Val Gly Gly Asn Glu Leu Val Phe Gln Val Lys Thr<br>450 455 460 | | | | 1394 |
| ctg tcc ctg cca gtg gtg gtg atc gtt cat ggc agc cag gac aac aat<br>Leu Ser Leu Pro Val Val Val Ile Val His Gly Ser Gln Asp Asn Asn<br>465 470 475 | | | | 1442 |
| gcg acg gcc act gtt ctc tgg gac aat gct ttt gca gag cct ggc agg<br>Ala Thr Ala Thr Val Leu Trp Asp Asn Ala Phe Ala Glu Pro Gly Arg<br>480 485 490 | | | | 1490 |
| gtg cca ttt gcc gtg cct gac aaa gtg ctg tgg cca cag ctg tgt gag<br>Val Pro Phe Ala Val Pro Asp Lys Val Leu Trp Pro Gln Leu Cys Glu<br>495 500 505 | | | | 1538 |
| gcg ctc aac atg aaa ttc aag gcc gaa gtg cag agc aac cgg ggc ctg<br>Ala Leu Asn Met Lys Phe Lys Ala Glu Val Gln Ser Asn Arg Gly Leu<br>510 515 520 525 | | | | 1586 |
| acc aag gag aac ctc gtg ttc ctg gcg cag aaa ctg ttc aac aac agc<br>Thr Lys Glu Asn Leu Val Phe Leu Ala Gln Lys Leu Phe Asn Asn Ser<br>530 535 540 | | | | 1634 |
| agc agc cac ctg gag gac tac agt ggc ctg tct gtg tcc tgg tcc cag | | | | 1682 |

-continued

| | | |
|---|---|---|
| Ser Ser His Leu Glu Asp Tyr Ser Gly Leu Ser Val Ser Trp Ser Gln<br>    545                      550                  555 | | |
| ttc aac agg gag aat tta cca gga cgg aat tac act ttc tgg caa tgg<br>Phe Asn Arg Glu Asn Leu Pro Gly Arg Asn Tyr Thr Phe Trp Gln Trp<br>           560                      565                  570 | 1730 |
| ttt gac ggt gtg atg gaa gtg tta aaa aaa cat ctc aag cct cat tgg<br>Phe Asp Gly Val Met Glu Val Leu Lys Lys His Leu Lys Pro His Trp<br>575                    580                      585 | 1778 |
| aat gat ggg gcc att ttg ggg ttt gta aac aag caa cag gcc cat gac<br>Asn Asp Gly Ala Ile Leu Gly Phe Val Asn Lys Gln Gln Ala His Asp<br>590                 595                      600                605 | 1826 |
| cta ctc att aac aag cca gat ggg acc ttc ctc ctg aga ttc agt gac<br>Leu Leu Ile Asn Lys Pro Asp Gly Thr Phe Leu Leu Arg Phe Ser Asp<br>           610                      615                  620 | 1874 |
| tca gaa att ggc ggc atc acc att gct tgg aag ttt gat tct cag gaa<br>Ser Glu Ile Gly Gly Ile Thr Ile Ala Trp Lys Phe Asp Ser Gln Glu<br>                  625                      630                  635 | 1922 |
| aga atg ttt tgg aat ctg atg cct ttt acc acc aga gac ttc tcc atc<br>Arg Met Phe Trp Asn Leu Met Pro Phe Thr Thr Arg Asp Phe Ser Ile<br>           640                      645                  650 | 1970 |
| cgg tcc cta gcc gac cgc ttg gga gac ttg aat tac ctt atc tac gtg<br>Arg Ser Leu Ala Asp Arg Leu Gly Asp Leu Asn Tyr Leu Ile Tyr Val<br>                  655                      660                  665 | 2018 |
| ttt cct gat cgg cca aaa gat gaa gta tac tcc aaa tac tac aca cca<br>Phe Pro Asp Arg Pro Lys Asp Glu Val Tyr Ser Lys Tyr Tyr Thr Pro<br>670                    675                      680                685 | 2066 |
| gtt ccc tgc gag tct gct act gct aaa gct gtt gat gga tac gtg aag<br>Val Pro Cys Glu Ser Ala Thr Ala Lys Ala Val Asp Gly Tyr Val Lys<br>                  690                      695                  700 | 2114 |
| cca cag atc aag caa gtg gtc cct gag ttt gtg aac gca tct gca gat<br>Pro Gln Ile Lys Gln Val Val Pro Glu Phe Val Asn Ala Ser Ala Asp<br>           705                      710                  715 | 2162 |
| gcc ggg ggc ggc agc gcc acg tac atg gac cag gcc ccc tcc cca gct<br>Ala Gly Gly Gly Ser Ala Thr Tyr Met Asp Gln Ala Pro Ser Pro Ala<br>                  720                      725                  730 | 2210 |
| gtg tgt ccc cag gct cac tat aac atg tac cca cag aac cct gac tca<br>Val Cys Pro Gln Ala His Tyr Asn Met Tyr Pro Gln Asn Pro Asp Ser<br>           735                      740                  745 | 2258 |
| gtc ctt gac acc gat ggg gac ttc gat ctg gag gac aca atg gac gta<br>Val Leu Asp Thr Asp Gly Asp Phe Asp Leu Glu Asp Thr Met Asp Val<br>750                    755                      760                765 | 2306 |
| gcg cgg cgt gtg gag gag ctc ctg ggc cgg cca atg gac agt cag tgg<br>Ala Arg Arg Val Glu Glu Leu Leu Gly Arg Pro Met Asp Ser Gln Trp<br>           770                      775                  780 | 2354 |
| atc ccg cac gca caa tcg tga ccccgcgacc tctccatctt cagcttcttc<br>Ile Pro His Ala Gln Ser *<br>           785 | 2405 |
| atcttcacca gaggaatcac tcttgtggat gttttaattc catcaatcgc ttctcttttg | 2465 |
| aaaacaatac tcataatgtg aagtgttaat actagttgtg accttagtgt ttctgtgcat | 2525 |
| ggtggcacca gcgaagggga gtgcgagtat gtgtttgtgt gtgtgtgtgt gtgtgtgtgt | 2585 |
| gtgtgcgtgt ttgcacgtta tggtgtttct ccctctcact gtctgagagt ttagttgtag | 2645 |
| cagaggggcc acagacagaa gctgtggtgg tttttacttt gtgcaaaaag gcagtgagtt | 2705 |
| tcgtgaagcc t | 2716 |

<210> SEQ ID NO 152
<211> LENGTH: 25
<212> TYPE: DNA

```
<213> ORGANISM: Artificial Sequence
<220> FEATURE:
<223> OTHER INFORMATION: PCR Primer

<400> SEQUENCE: 152
cttcatcttc accagaggaa tcact                                          25

<210> SEQ ID NO 153
<211> LENGTH: 30
<212> TYPE: DNA
<213> ORGANISM: Artificial Sequence
<220> FEATURE:
<223> OTHER INFORMATION: PCR Primer

<400> SEQUENCE: 153
cttcacatta tgagtattgt ttcaaaagag                                     30

<210> SEQ ID NO 154
<211> LENGTH: 25
<212> TYPE: DNA
<213> ORGANISM: Artificial Sequence
<220> FEATURE:
<223> OTHER INFORMATION: PCR Probe

<400> SEQUENCE: 154
tgtggatgtt ttaattccat gaatc                                          25

<210> SEQ ID NO 155
<211> LENGTH: 20
<212> TYPE: DNA
<213> ORGANISM: Artificial Sequence
<220> FEATURE:
<223> OTHER INFORMATION: Antisense Compound

<400> SEQUENCE: 155
tctcggccag ctccacgcgg                                                20

<210> SEQ ID NO 156
<211> LENGTH: 20
<212> TYPE: DNA
<213> ORGANISM: Artificial Sequence
<220> FEATURE:
<223> OTHER INFORMATION: Antisense Compound

<400> SEQUENCE: 156
cctcggccag catctcctcc                                                20

<210> SEQ ID NO 157
<211> LENGTH: 20
<212> TYPE: DNA
<213> ORGANISM: Artificial Sequence
<220> FEATURE:
<223> OTHER INFORMATION: Antisense Compound

<400> SEQUENCE: 157
tgtccgtgat ggtggcgttg                                                20

<210> SEQ ID NO 158
<211> LENGTH: 20
<212> TYPE: DNA
<213> ORGANISM: Artificial Sequence
<220> FEATURE:
<223> OTHER INFORMATION: Antisense Compound

<400> SEQUENCE: 158
ggatcctcag gctctcctgg                                                20
```

```
<210> SEQ ID NO 159
<211> LENGTH: 20
<212> TYPE: DNA
<213> ORGANISM: Artificial Sequence
<220> FEATURE:
<223> OTHER INFORMATION: Antisense Compound

<400> SEQUENCE: 159
gacacctgct tctgctggag                                               20

<210> SEQ ID NO 160
<211> LENGTH: 20
<212> TYPE: DNA
<213> ORGANISM: Artificial Sequence
<220> FEATURE:
<223> OTHER INFORMATION: Antisense Compound

<400> SEQUENCE: 160
ggtctgctgc ttccgcagca                                               20

<210> SEQ ID NO 161
<211> LENGTH: 20
<212> TYPE: DNA
<213> ORGANISM: Artificial Sequence
<220> FEATURE:
<223> OTHER INFORMATION: Antisense Compound

<400> SEQUENCE: 161
catctcctcc actgggccgg                                               20

<210> SEQ ID NO 162
<211> LENGTH: 20
<212> TYPE: DNA
<213> ORGANISM: Artificial Sequence
<220> FEATURE:
<223> OTHER INFORMATION: Antisense Compound

<400> SEQUENCE: 162
gcaaacttgg tctgggtctt                                               20

<210> SEQ ID NO 163
<211> LENGTH: 20
<212> TYPE: DNA
<213> ORGANISM: Artificial Sequence
<220> FEATURE:
<223> OTHER INFORMATION: Antisense Compound

<400> SEQUENCE: 163
acggcaaatg gcaccctgcc                                               20

<210> SEQ ID NO 164
<211> LENGTH: 20
<212> TYPE: DNA
<213> ORGANISM: Artificial Sequence
<220> FEATURE:
<223> OTHER INFORMATION: Antisense Compound

<400> SEQUENCE: 164
cctggtccat gtacgtggcg                                               20

<210> SEQ ID NO 165
<211> LENGTH: 20
<212> TYPE: DNA
<213> ORGANISM: Artificial Sequence
<220> FEATURE:
```

<223> OTHER INFORMATION: Antisense Compound

<400> SEQUENCE: 165
ccgcttcaca ttgcatattg                                           20

<210> SEQ ID NO 166
<211> LENGTH: 20
<212> TYPE: DNA
<213> ORGANISM: Artificial Sequence
<220> FEATURE:
<223> OTHER INFORMATION: Antisense Compound

<400> SEQUENCE: 166
cgaccgcttc acattgcata                                           20

<210> SEQ ID NO 167
<211> LENGTH: 20
<212> TYPE: DNA
<213> ORGANISM: Artificial Sequence
<220> FEATURE:
<223> OTHER INFORMATION: Antisense Compound

<400> SEQUENCE: 167
tgcacaagga cacacacaca                                           20

<210> SEQ ID NO 168
<211> LENGTH: 20
<212> TYPE: DNA
<213> ORGANISM: Artificial Sequence
<220> FEATURE:
<223> OTHER INFORMATION: Antisense Compound

<400> SEQUENCE: 168
ggcgtagctc atgcacaagg                                           20

<210> SEQ ID NO 169
<211> LENGTH: 20
<212> TYPE: DNA
<213> ORGANISM: Artificial Sequence
<220> FEATURE:
<223> OTHER INFORMATION: Antisense Compound

<400> SEQUENCE: 169
gccacatccc aggactgcac                                           20

<210> SEQ ID NO 170
<211> LENGTH: 20
<212> TYPE: DNA
<213> ORGANISM: Artificial Sequence
<220> FEATURE:
<223> OTHER INFORMATION: Antisense Compound

<400> SEQUENCE: 170
tgcagtgaca gaggctcggt                                           20

<210> SEQ ID NO 171
<211> LENGTH: 20
<212> TYPE: DNA
<213> ORGANISM: Artificial Sequence
<220> FEATURE:
<223> OTHER INFORMATION: Antisense Compound

<400> SEQUENCE: 171
ggaggaatag gtctggctgc                                           20

```
<210> SEQ ID NO 172
<211> LENGTH: 20
<212> TYPE: DNA
<213> ORGANISM: Artificial Sequence
<220> FEATURE:
<223> OTHER INFORMATION: Antisense Compound

<400> SEQUENCE: 172
gggcccagga ggataggtc                                                  20

<210> SEQ ID NO 173
<211> LENGTH: 20
<212> TYPE: DNA
<213> ORGANISM: Artificial Sequence
<220> FEATURE:
<223> OTHER INFORMATION: Antisense Compound

<400> SEQUENCE: 173
ggcaaagctt ctcactccgg                                                 20

<210> SEQ ID NO 174
<211> LENGTH: 20
<212> TYPE: DNA
<213> ORGANISM: Artificial Sequence
<220> FEATURE:
<223> OTHER INFORMATION: Antisense Compound

<400> SEQUENCE: 174
acgcgctctc atagggttca                                                 20

<210> SEQ ID NO 175
<211> LENGTH: 20
<212> TYPE: DNA
<213> ORGANISM: Artificial Sequence
<220> FEATURE:
<223> OTHER INFORMATION: Antisense Compound

<400> SEQUENCE: 175
tgctaaggac atggccgggc                                                 20

<210> SEQ ID NO 176
<211> LENGTH: 20
<212> TYPE: DNA
<213> ORGANISM: Artificial Sequence
<220> FEATURE:
<223> OTHER INFORMATION: Antisense Compound

<400> SEQUENCE: 176
aaccctcact caaaccggcg                                                 20

<210> SEQ ID NO 177
<211> LENGTH: 20
<212> TYPE: DNA
<213> ORGANISM: Artificial Sequence
<220> FEATURE:
<223> OTHER INFORMATION: Antisense Compound

<400> SEQUENCE: 177
gccaagcagc caagcaagga                                                 20

<210> SEQ ID NO 178
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 178
aaacgtgggc aacagcatca                                          20

<210> SEQ ID NO 179
<211> LENGTH: 20
<212> TYPE: DNA
<213> ORGANISM: Artificial Sequence
<220> FEATURE:
<223> OTHER INFORMATION: Antisense Compound

<400> SEQUENCE: 179
gagaggcaag caaagaaggc                                          20

<210> SEQ ID NO 180
<211> LENGTH: 20
<212> TYPE: DNA
<213> ORGANISM: Artificial Sequence
<220> FEATURE:
<223> OTHER INFORMATION: Antisense Compound

<400> SEQUENCE: 180
cccaccatat cctagaccca                                          20

<210> SEQ ID NO 181
<211> LENGTH: 20
<212> TYPE: DNA
<213> ORGANISM: Artificial Sequence
<220> FEATURE:
<223> OTHER INFORMATION: Antisense Compound

<400> SEQUENCE: 181
cctgtccacc caccatatcc                                          20

<210> SEQ ID NO 182
<211> LENGTH: 20
<212> TYPE: DNA
<213> ORGANISM: Artificial Sequence
<220> FEATURE:
<223> OTHER INFORMATION: Antisense Compound

<400> SEQUENCE: 182
ggaggcaaga ggaccaaccc                                          20

<210> SEQ ID NO 183
<211> LENGTH: 20
<212> TYPE: DNA
<213> ORGANISM: Artificial Sequence
<220> FEATURE:
<223> OTHER INFORMATION: Antisense Compound

<400> SEQUENCE: 183
ccaggaggca agaggaccaa                                          20

<210> SEQ ID NO 184
<211> LENGTH: 20
<212> TYPE: DNA
<213> ORGANISM: Artificial Sequence
<220> FEATURE:
<223> OTHER INFORMATION: Antisense Compound

<400> SEQUENCE: 184
ccagattcca caggcacgca                                          20

<210> SEQ ID NO 185
<211> LENGTH: 20
```

```
<212> TYPE: DNA
<213> ORGANISM: Artificial Sequence
<220> FEATURE:
<223> OTHER INFORMATION: Antisense Compound

<400> SEQUENCE: 185
ccagcggagt caaaccagat                                                    20

<210> SEQ ID NO 186
<211> LENGTH: 20
<212> TYPE: DNA
<213> ORGANISM: Artificial Sequence
<220> FEATURE:
<223> OTHER INFORMATION: Antisense Compound

<400> SEQUENCE: 186
gcctcaccag aacacagcca                                                    20

<210> SEQ ID NO 187
<211> LENGTH: 20
<212> TYPE: DNA
<213> ORGANISM: Artificial Sequence
<220> FEATURE:
<223> OTHER INFORMATION: Antisense Compound

<400> SEQUENCE: 187
tcttccatgg tcagctgccc                                                    20

<210> SEQ ID NO 188
<211> LENGTH: 20
<212> TYPE: DNA
<213> ORGANISM: Artificial Sequence
<220> FEATURE:
<223> OTHER INFORMATION: Antisense Compound

<400> SEQUENCE: 188
gggctctcaa tcttccatgg                                                    20

<210> SEQ ID NO 189
<211> LENGTH: 20
<212> TYPE: DNA
<213> ORGANISM: Artificial Sequence
<220> FEATURE:
<223> OTHER INFORMATION: Antisense Compound

<400> SEQUENCE: 189
cacagccatg gtttacccgg                                                    20

<210> SEQ ID NO 190
<211> LENGTH: 20
<212> TYPE: DNA
<213> ORGANISM: Artificial Sequence
<220> FEATURE:
<223> OTHER INFORMATION: Antisense Compound

<400> SEQUENCE: 190
tgccgcacct caatgggaaa                                                    20

<210> SEQ ID NO 191
<211> LENGTH: 20
<212> TYPE: DNA
<213> ORGANISM: Artificial Sequence
<220> FEATURE:
<223> OTHER INFORMATION: Antisense Compound

<400> SEQUENCE: 191
```

-continued

| | |
|---|---|
| ggacatggca tcagcaaggc | 20 |

<210> SEQ ID NO 192
<211> LENGTH: 20
<212> TYPE: DNA
<213> ORGANISM: Artificial Sequence
<220> FEATURE:
<223> OTHER INFORMATION: Antisense Compound

<400> SEQUENCE: 192

| | |
|---|---|
| ctgcttctgc tggagggccg | 20 |

<210> SEQ ID NO 193
<211> LENGTH: 20
<212> TYPE: DNA
<213> ORGANISM: Artificial Sequence
<220> FEATURE:
<223> OTHER INFORMATION: Antisense Compound

<400> SEQUENCE: 193

| | |
|---|---|
| tgcaaccagg cctccagaga | 20 |

<210> SEQ ID NO 194
<211> LENGTH: 20
<212> TYPE: DNA
<213> ORGANISM: Artificial Sequence
<220> FEATURE:
<223> OTHER INFORMATION: Antisense Compound

<400> SEQUENCE: 194

| | |
|---|---|
| tcttctggtg cttctcggcc | 20 |

<210> SEQ ID NO 195
<211> LENGTH: 20
<212> TYPE: DNA
<213> ORGANISM: Artificial Sequence
<220> FEATURE:
<223> OTHER INFORMATION: Antisense Compound

<400> SEQUENCE: 195

| | |
|---|---|
| tcggccaact tctcacacca | 20 |

<210> SEQ ID NO 196
<211> LENGTH: 20
<212> TYPE: DNA
<213> ORGANISM: Artificial Sequence
<220> FEATURE:
<223> OTHER INFORMATION: Antisense Compound

<400> SEQUENCE: 196

| | |
|---|---|
| atctcctcca ctgggccggg | 20 |

<210> SEQ ID NO 197
<211> LENGTH: 20
<212> TYPE: DNA
<213> ORGANISM: Artificial Sequence
<220> FEATURE:
<223> OTHER INFORMATION: Antisense Compound

<400> SEQUENCE: 197

| | |
|---|---|
| gccactgtaa tcattgcggg | 20 |

<210> SEQ ID NO 198
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 198
ccagctcatt tccaccaaca                                               20

<210> SEQ ID NO 199
<211> LENGTH: 20
<212> TYPE: DNA
<213> ORGANISM: Artificial Sequence
<220> FEATURE:
<223> OTHER INFORMATION: Antisense Compound

<400> SEQUENCE: 199
cgtcgcattg ttgtcctggc                                               20

<210> SEQ ID NO 200
<211> LENGTH: 20
<212> TYPE: DNA
<213> ORGANISM: Artificial Sequence
<220> FEATURE:
<223> OTHER INFORMATION: Antisense Compound

<400> SEQUENCE: 200
gcactttgtc aggcacggca                                               20

<210> SEQ ID NO 201
<211> LENGTH: 20
<212> TYPE: DNA
<213> ORGANISM: Artificial Sequence
<220> FEATURE:
<223> OTHER INFORMATION: Antisense Compound

<400> SEQUENCE: 201
ggtggctgct gctgttgttg                                               20

<210> SEQ ID NO 202
<211> LENGTH: 20
<212> TYPE: DNA
<213> ORGANISM: Artificial Sequence
<220> FEATURE:
<223> OTHER INFORMATION: Antisense Compound

<400> SEQUENCE: 202
ccaggacaca gacaggccac                                               20

<210> SEQ ID NO 203
<211> LENGTH: 20
<212> TYPE: DNA
<213> ORGANISM: Artificial Sequence
<220> FEATURE:
<223> OTHER INFORMATION: Antisense Compound

<400> SEQUENCE: 203
gggaccagga cacagacagg                                               20

<210> SEQ ID NO 204
<211> LENGTH: 20
<212> TYPE: DNA
<213> ORGANISM: Artificial Sequence
<220> FEATURE:
<223> OTHER INFORMATION: Antisense Compound

<400> SEQUENCE: 204
ggtcatgggc ctgttgcttg                                               20
```

```
<210> SEQ ID NO 205
<211> LENGTH: 20
<212> TYPE: DNA
<213> ORGANISM: Artificial Sequence
<220> FEATURE:
<223> OTHER INFORMATION: Antisense Compound

<400> SEQUENCE: 205
tgccgccaat ttctgagtca                                                    20

<210> SEQ ID NO 206
<211> LENGTH: 20
<212> TYPE: DNA
<213> ORGANISM: Artificial Sequence
<220> FEATURE:
<223> OTHER INFORMATION: Antisense Compound

<400> SEQUENCE: 206
ttcaagtctc ccaagcggtc                                                    20

<210> SEQ ID NO 207
<211> LENGTH: 20
<212> TYPE: DNA
<213> ORGANISM: Artificial Sequence
<220> FEATURE:
<223> OTHER INFORMATION: Antisense Compound

<400> SEQUENCE: 207
aattcaagtc tcccaagcgg                                                    20

<210> SEQ ID NO 208
<211> LENGTH: 20
<212> TYPE: DNA
<213> ORGANISM: Artificial Sequence
<220> FEATURE:
<223> OTHER INFORMATION: Antisense Compound

<400> SEQUENCE: 208
tggccgatca ggaaacacgt                                                    20

<210> SEQ ID NO 209
<211> LENGTH: 20
<212> TYPE: DNA
<213> ORGANISM: Artificial Sequence
<220> FEATURE:
<223> OTHER INFORMATION: Antisense Compound

<400> SEQUENCE: 209
ccattgtgtc ctccagatcg                                                    20

<210> SEQ ID NO 210
<211> LENGTH: 20
<212> TYPE: DNA
<213> ORGANISM: Artificial Sequence
<220> FEATURE:
<223> OTHER INFORMATION: Antisense Compound

<400> SEQUENCE: 210
tgactgtcca ttggccggcc                                                    20

<210> SEQ ID NO 211
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 211
tgcgggatcc actgactgtc                                        20

<210> SEQ ID NO 212
<211> LENGTH: 20
<212> TYPE: DNA
<213> ORGANISM: Artificial Sequence
<220> FEATURE:
<223> OTHER INFORMATION: Antisense Compound

<400> SEQUENCE: 212
tgaagatgga gaggtcgcgg                                        20

<210> SEQ ID NO 213
<211> LENGTH: 20
<212> TYPE: DNA
<213> ORGANISM: Artificial Sequence
<220> FEATURE:
<223> OTHER INFORMATION: Antisense Compound

<400> SEQUENCE: 213
gccaccatgc acagaaacac                                        20
```

MODULATION OF STAT5 EXPRESSION

FIELD OF THE DISCLOSURE

Compositions and methods for modulating the expression of STAT5 are described herein. In particular, the present application relates to antisense compounds, particularly oligonucleotide compounds, which, in preferred embodiments, hybridize with nucleic acid molecules encoding STAT5. Such compounds are shown herein to modulate the expression of STAT5.

BACKGROUND INFORMATION

Many important cellular processes are regulated by cytokines, hormones and growth factors which interact with cell-surface receptors. Signal transducer and activator of transcription (STAT) proteins play a crucial role in coordinating the response of cells to cytokine receptor stimulation by acting as cytosolic messengers and nuclear transcription factors. Upon cytokine stimulation, STATs are phosphorylated on a conserved tyrosine residue. This phosphorylation can be catalyzed by the Janus (JAK) family kinases, intrinsic cellular receptor kinases or other cellular tyrosine kinases. Activated, phosphorylated STATs then dimerize and translocate to the nucleus, where they bind to DNA or act with other DNA binding proteins in multiprotein complexes. These complexes regulate gene transcription in a affects a wide range of biological processes, including cell growth and differentiation, the immune response, antiviral activity, and homeostasis (Grimley et al., *Cytokine Growth Factor Rev.*, 1999, 10, 131–157; Lin et al., *Oncogene*, 2000, 19, 2496–2504).

The STATs were originally discovered as critical players in interferon signaling mediated by cytokine receptors lacking intrinsic tyrosine kinase domains and employing the JAK kinases. To date, seven STAT family members have been described: STAT1, STAT2, STAT3, STAT4, STAT5A, STAT5B and STAT6 (Bromberg, *J. Clin. Invest.*, 2002, 109, 1139–1142). STAT5A (also known as mammary gland factor, MGF) and STAT5B are two distinctly encoded proteins. STAT5A was originally identified as the prolactin-stimulated ovine gland mammary gland factor (Wakao et al., *Embo J.*, 1994, 13, 2182–2191), but was subsequently characterized as member of the STAT family when it was identified as an interleukin-2 induced STAT protein (Hou et al., *Immunity*, 1995, 2, 321–329). STAT5B was identified as an additional member of the STAT family that is similarly induced by interleukin-2 (Lin et al., *J. Biol. Chem.*, 1996, 271, 10738–10744). Human STAT5A and STAT5B are both localized to chromosome 17 in the band 17q11.2 and have a very similar genomic organization (Ambrosio et al., *Gene*, 2002, 285, 311–318; Lin et al., *J. Biol. Chem.*, 1996, 271, 10738–10744). Human STAT5A and STAT5B share 91% identity at the amino acid level (Lin et al., *J. Biol. Chem.*, 1996, 271, 10738–10744).

STAT5A and STAT5B transcripts are ubiquitously expressed in human tissues, including spleen, stomach, brain, skeletal muscle, liver, kidney, lung, placenta, pancreas, heart and small intestine (Ambrosio et al., *Gene*, 2002, 285, 311–318). STAT5 is activated in response to a variety of cytokines, hormones and growth factors, including prolactin, various interleukins, erythropoietin and granulocyte macrophage-colony stimulating factor. STAT5 has been implicated in transducing signals that affect cell proliferation, differentiation and apoptosis, particularly in the processes of hematopoiesis and immunoregulation, reproduction and lipid metabolism (Grimley et al., *Cytokine Growth Factor Rev.*, 1999, 10, 131–157).

While STAT5A and STAT5B share a high degree of sequence homology, each STAT5 has distinct biological functions. STAT5A-deficient mice develop normally, but mammary lobuloalveolar outgrowth during pregnancy is reduced, and female mice fail to lactate after parturition due to defects in mammary gland differentiation (Liu et al., *Genes Dev.*, 1997, 11, 179–186). These results demonstrate that STAT5A is essential for adult mammary gland development and lactogenesis. Targeted disruption of the murine STAT5B gene leads to a striking loss of multiple, sexually differentiated responses associated with the sexually dimorphic pattern of pituitary growth hormone secretion. Male STAT5B-deficient mice exhibit body growth rates and male-specific liver gene expression levels that are decreased relative to wild-type female levels, suggesting that STAT5B is necessary for the physiological effects of male growth hormone on body growth rate and liver gene expression. Only a modest decrease in growth rate is seen in STAT5B-deficient females (Udy et al., *Proc. Natl. Acad. Sci. USA*, 1997, 94, 7239–7244). The phenotypes of the gene disrupted mice correlate with the patterns of expression, with STAT5A highly abundant in mouse mammary tissue during lactation and STAT5B highly abundant in muscle tissue of virgin and lactating female mice and in male mice (Liu et al., *Proc. Natl. Acad. Sci. USA*, 1995, 92, 8831–8835).

Disruption of both STAT5A and STAT5B results in the phenotypes associated with disruption of each individual gene and also reveals that the STAT5 proteins have redundant functions in response to growth hormone and prolactin. Mice deficient in both STAT5A and STAT5B are smaller than their wild-type littermates, and the females are infertile. Peripheral T cells from these mice are unable to proliferate in response to T cell receptor engagement and interleukin-2, suggesting that STAT5 plays a role in T cell regulation (Teglund et al., *Cell*, 1998, 93, 841–850).

Each STAT5 gene gives rise to both long and short isoforms. These functionally distinct isoforms, which are activated in distinct populations of cells, are generated not by RNA processing but by STAT5-cleaving protease activity, also limited to distinct populations of cells. Interleukin-3 activates full-length STAT5A and STAT5B in mature myeloid cell lines and the c-terminally truncated forms in more immature myeloid cell lines (Azam et al., *Immunity*, 1997, 6, 691–701). These naturally occurring truncated variants can inhibit full-length STAT5 function in cultured mammalian cells but do not affect cell growth rate (Moriggl et al., *Mol. Cell. Biol.*, 1996, 16, 5691–5700; Wang et al., *Mol. Cell. Biol.*, 1996, 16, 6141–6148). Additionally, an alternatively spliced form of human STAT5B exists, which uses an alternative promoter and 5' exon within the STAT5B gene. This STAT5B transcript is found only in placenta tissue (Ambrosio et al., *Gene*, 2002, 285, 311–318). Alternatively spliced forms of rat STAT5A have been isolated from rat mammary gland, and are designated STAT5A1 and STAT5A2 (Kazansky et al., *Mol. Endocrinol.*, 1995, 9, 1598–1609). A STAT5B isoform that lacks the COOH-terminal 40 amino acids has been isolated from rat liver and designated STAT5BΔ40C (Ripperger et al., *J. Biol. Chem.*, 1995, 270, 29998–30006).

The STAT proteins are not known to contribute directly to cell cycle checkpoint regulation or DNA repair. However, they contribute to tumorigenesis through their involvement in growth factor signaling, apoptosis and angiogenesis. Additionally, because this transcription factor family participates in the immune response, defective STAT activity can compromise immune surveillance and thus promote cancer cell survival. STAT5 is commonly found constitutively activated in several cancers. To date, the most common mechanism for constitutive phosphorylation and activation of STAT proteins is excessive JAK kinase activity (Bromberg, *J. Clin. Invest.*, 2002, 109, 1139–1142).

A role for STAT5 in the process of tumor initiation and progression is demonstrated by the link between constitutive STAT5 activity and cultured cell transformation. STAT5 activation is sufficient for transformation of hematopoietic precursor cells (Spiekermann et al., *Exp. Hematol.*, 2002, 30, 262–271). Both STAT5A and STAT5B are constitutively phosphorylated and are transcriptionally active in K562 leukemia cells (Carlesso et al., *J. Exp. Med.*, 1996, 183, 811–820; de Groot et al., *Blood*, 1999, 94, 1108–1112; Weber-Nordt et al., *Blood*, 1996, 88, 809–816). Additionally, increased constitutive activation of STAT5 was detected in transformed human squamous epithelial cells derived from squamous cell carcinomas of the head and neck. Targeting of STAT5B, but not STAT5A, with antisense oligonucleotides inhibited the growth of these squamous epithelial cells (Leong et al., *Oncogene*, 2002, 21, 2846–2853).

Abnormal STAT5 activity is indeed found associated with many cancers, particularly hematopoietic malignancies. Constitutively activated STAT5 is found in cell samples taken from patients with T-cell and B-cell acute lymphoblastic leukemia (ALL), adult T-cell leukemia/lymphoma (ATLL), adult T-cell leukemia (ATL), acute myeloid leukemia (AML), chronic myelocytic leukemia (CML) and acute promyelocytic-like leukemia (APL-L) (Arnould et al., *Hum. Mol. Genet.*, 1999, 8, 1741–1749; Carlesso et al., *J. Exp. Med.*, 1996, 183, 811–820; Chai et al., *J Immunol.*, 1997, 159, 4720–4728; Gouilleux-Gruart et al., *Blood*, 1996, 87, 1692–1697; Spiekermann et al., *Clin. Cancer Res.*, 2003, 9, 2140–2150; Takemoto et al., *Proc. Nati. Acad. Sci. USA*, 1997, 94, 13897–13902; Weber-Nordt et al., *Blood*, 1996, 88, 809–816). Collectively, these data demonstrate the involvement of activated STAT5 in hematopoietic cancers.

One mechanism by which constitutively activated STAT5 may promote cancer cell survival is through the inhibition of apoptosis. Introduction of a constitutively activated STAT5 protects murine T lymphoma cells against dexamethasone-induced apoptosis (Demoulin et al., *J. Biol. Chem.*, 1999, 274, 25855–25861). Conversely, blocking of tyrosine kinase signaling using a small molecule inhibitor in cells which express BCR/ABL, a constitutively active tyrosine kinase, inhibited cell growth and induced apoptosis (Donato et al., *Blood*, 2001, 97, 2846–2853; Huang et al., *Oncogene*, 2002, 21, 8804–8816). Apoptosis was correlated with the inhibition of STAT5 activation. Viral delivery of a dominantly acting STAT5 mutant to CML primary cells, a CML cell line or prostate cancer cells induces cell death, consistent with a role of STAT5 signaling in growth and survival of cancer cells (Ahonen et al., *J. Biol. Chem.*, 2003; Huang et al., *Oncogene*, 2002, 21, 8804–8816).

Inappropriate activation of STAT proteins may also allow cancer cells to survive and proliferate in the absence of cytokines and growth factors. STAT5 activation is often observed in correlation with the presence the BCR/ABL chimeric oncogene that results from a chromosomal translocation. The BCR/ABL fusion is found in both CML and ALL (Coffer et al., *Oncogene*, 2000, 19, 2511–2522). STAT5 activation in cells derived from CML patients is strictly dependent on BCR/ABL kinase activity and strongly correlates with its ability to confer cytokine independent growth in hematopoietic cells (Carlesso et al., *J. Exp. Med.*, 1996, 183, 811–820; Shuai et al., *Oncogene*, 1996, 13, 247–254).

Constitutively activated STAT5 is also found in several CML-derived cell lines expressing BCR/ABL. Furthermore, BCR/ABL is expressed in peripheral blood cells from patients with AML, and constitutively activated STAT5 was found in one of these AML patients (Chai et al., *J. Immunol.*, 1997, 159, 4720–4728). Both the alpha and beta isoforms of STAT5A and STAT5B are found expressed in cells from AML patients and are proposed to be due to alternative mRNA splicing rather than to proteolytic cleavage (Xia et al., *Cancer Res.*, 1998, 58, 3173–3180). Additionally, STAT5 is a major target of other leukemic fusion proteins with protein tyrosine kinase activity, including the TEL-JAK2 and TEL-ABL fusion proteins, which act to inappropriately activate STAT5 (Spiekermann et al., *Exp. Hematol.*, 2002, 30, 262–271).

A case of acute promyelocytic-like leukemia (APL-L) exhibits a structurally abnormal STAT gene that is the result of a fusion between the retinoic acid receptor alpha (RARA) gene and the STAT5B gene. Whereas STAT5B under normal circumstances is translocated to the nucleus only upon tyrosine kinase activation, the STAT5B/RARA fusion is mislocalized in the nucleus (Arnould et al., *Hum. Mol. Genet.*, 1999, 8, 1741–1749). The fusion protein enhances STAT3 activity, which is a characteristic shared by other APL fusion proteins (Dong and Tweardy, *Blood*, 2002, 99, 2637–2646).

Phosphorothioate antisense oligodeoxynucleotides, 24 nucleotides in length, complementary to the start codon of either STAT5A or STAT5B, were used to inhibit STAT5A and STAT5B expression for the purpose of investigating their role in normal hematopoiesis. Downregulation of STAT5A or STAT5B following antisense oligodeoxynucleotide treatment had no effect on the viability, clonogenecity and apoptosis of cord blood hematopoietic cells (Baskiewicz-Masiuk et al., *Cell Mol. Biol. Lett.*, 2003, 8, 317–331).

The U.S. Pat. No. 5,534,409 discloses and claims an isolated DNA which has at least about 90% sequence identity to a nucleotide sequence encoding mammary gland growth factor (MGF), also known as STAT5. Also disclosed are oligonucleotides useful for hybridization for the purpose of isolating cDNA clones encoding MGF (Groner et al., 1996).

The U.S. Pat. No. 5,618,693 claims and discloses an isolated nucleic acid encoding a human STAT5 (hSTAT5). Generally disclosed are nucleic acids for use as hybridization probes, PCR primers and therapeutic nucleic acids, whereby hStat5 nucleic acids are used to modulate, usually reduce, cellular expression or intracellular concentration or availability of active hStat5 and whereby these therapeutic nucleic acids are typically antisense nucleic acids (McKnight et al., 1997).

Disclosed and claimed in the U.S. Pat. No. 6,160,092 is a crystal of the core protein of the STAT protein in dimeric form with an 18-mer duplex DNA that contains a binding site for the STAT dimer, as well as methods of using the structural information in drug discovery and drug development. Also disclosed are nucleic acid molecules encoding STAT5A, including RNA and DNA molecules and hybridizable nucleic acid molecules with minimum length of 12 nucleotides (Chen et al., 2000).

Disclosed in the U.S. Pat. No. 6,518,021 are nucleic acid molecules encoding a human STAT5A molecule, whereby a nucleic acid molecule is a DNA or RNA sequence or a PCR primer (Thastrup et al., 2003).

The PCT publication WO 02/46466 discloses and claims a method of inhibiting cellular proliferation mediated by a BRCA/STAT complex, comprising contacting a BRCA/STAT-containing cell with an effective amount of a BRCA/STAT complex modulating compound sufficient to modulate the amount or activity of a BRCA/STAT complex in said cell, wherein said BRCA/STAT complex modulating compound is selected from the group consisting of small molecule, polypeptide and nucleic acid. This application discloses that a BRCA/STAT complex modulating compound can be a nucleic acid, such as a DNA or RNA molecule, including antisense nucleic acids, that specifically binds to a BRCA or STAT nucleic acid (Valgeirsdottir, 2002).

The US Pre-grant publication 20030105057 claims and discloses a method wherein the amount of phosphorylated RECEPTOR/PTK-STAT pathway in a cell is altered by introducing into the cell nucleic acid molecules that encode RECEPTOR/PTK-STAT proteins, including STAT5A/B, to effect the increase or decrease of the expression and/or activation of a RECEPTOR or STAT, wherein the STAT can be STAT5A/B. This application further discloses methods whereby the amount of phosphorylated RECEPTOR/PTK-STAT protein is increased or decreased by introducing into the cell an antisense nucleic acid molecule that encodes a tyrosine kinase and/or a RECEPTOR/PTK-STAT protein (Fu et al., 2003).

SUMMARY

Described herein are antisense compounds, especially nucleic acid and nucleic acid-like oligomers, which are targeted to a nucleic acid encoding STAT5, and which modulate the expression of STAT5. Pharmaceutical and other compositions comprising these compounds are also provided. Further provided are methods of screening for modulators of STAT5 and methods of modulating the expression of STAT5 in cells, tissues or animals comprising contacting said cells, tissues or animals with one or more of the compounds or compositions described herein. Methods of treating an animal, particularly a human, suspected of having or being prone to a disease or condition associated with expression of STAT5 are also set forth herein. Such methods comprise administering a therapeutically or prophylactically effective amount of one or more of the compounds or compositions to the person in need of treatment. In another embodiment, the antisense compounds disclosed herein optionally exclude ISIS 130826.

DETAILED DESCRIPTION

A. Overview

The use of standard cytotoxic chemotherapy in the treatment of cancers, in particular leukemias, has reached a plateau; thus, there exists a need for novel therapies designed to such cancers. Antisense technology is an effective means for reducing the expression of specific gene products and is therefore useful in a number of therapeutic, diagnostic, and research applications for the modulation of STAT5 expression.

Described herein are compositions and methods for modulating STAT5 expression (STAT5A and/or STAT5B), including simultaneous modulation of both isoforms, STAT5A and STAT5B. This is accomplished by providing oligonucleotides which specifically hybridize with one or more nucleic acid molecules encoding STAT5A, STAT5B or both STAT5A and STAT5B. As described in more detail in the examples set forth herein, single oligonucleotides may be used to target STAT5A, STAT5B or both STAT5A and STAT5B. The oligonucleotides that target both isoforms bind to regions that similar nucleotide sequence in both isoforms. In one embodiment, the term "similar" indicates at least about 70%, 75%, 80%, 85%, 90% or >95% identity between the conserved regions in both isoforms.

The antisense oligonucleotides targeted to STAT5 are useful in treating various disorders arising from overexpression of STAT5 such as hyperproliferative disorders, including hematopoietic cancers such as T-cell and B-cell acute lymphoblastic leukemia (ALL), adult T-cell leukemia/lymphoma (ATLL), adult T-cell leukemia (ATL), acute mycloid leukemia (AML), chronic myelocytic leukemia (CML) and acute promyelocytic-like leukemia (APL-L), lymphomas and solid tumors of the prostate, breast, lung, stomach, intestine, head, neck, pancreas, liver, ovary and spleen.

As used herein, the terms "target nucleic acid" and "nucleic acid molecule encoding STAT5" have been used for convenience to encompass DNA encoding STAT5, RNA (including pre-mRNA and mRNA or portions thereof) transcribed from such DNA, and also cDNA derived from such RNA. The hybridization of a compound with its target nucleic acid is generally referred to as "antisense". Consequently, the preferred mechanism believed to be included in the practice of some embodiments is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of STAT5. As used herein, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

As used herein, "hybridization" means the pairing of complementary strands of oligomeric compounds. In the embodiments described herein, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the phrase "stringent hybridization conditions" or "stringent conditions" refers to conditions under which a compound will hybridize to its target sequence, but to a minimal number of other sequences. Stringent conditions are sequence-dependent and will be different in different circumstances and as described herein. "Stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds described herein comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the described embodiments. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403–410; Zhang and Madden, *Genome Res.*, 1997, 7, 649–656).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482–489). In some preferred embodiments, homology, sequence identity or complementarity, between the oligomeric and target is between about 50% to about 60%. In some embodiments, homology, sequence identity or complementarity, is between about 60% to about 70%. In preferred embodiments, homology, sequence identity or complementarity, is between about 70% and about 80%. In more preferred embodiments, homology, sequence identity or complementarity, is between about 80% and about 90%. In some preferred embodiments, homology, sequence identity or complementarity, is about 90%, about 92%, about 94%, about 95%, about 96%, about 97%, about 98%, about 99% or about 100%.

B. Compounds

As used herein, antisense compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell*, 1995, 81, 611–620). Montgomery et al. have shown that the primary interference effects of dsRNA are posttranscriptional (Montgomery et al., *Proc. Natl. Acad. Sci. USA*, 1998, 95, 15502–15507). The posttranscriptional antisense mechanism defined in Caenorhabditis elegans resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806–811). Recently, it has been shown that it is, in fact, the single-stranded RNA oligomers of antisense polarity of the dsRNAs which are the potent inducers of RNAi (Tijsterman et al., *Science*, 2002, 295, 694–697).

The antisense compounds also include modified compounds in which a different base is present at one or more of the nucleotide positions in the compound. For example, if the first nucleotide is an adenosine, modified compounds may be produced which contain thymidine, guanosine or cytidine at this position. This may be done at any of the positions of the antisense compound. These compounds are then tested using the methods described herein to determine their ability to inhibit expression of STAT5 mRNA.

As used herein, the term "oligomeric compound" refers to a polymer or oligomer comprising a plurality of monomeric units. As used herein, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of antisense compound, other families of antisense compounds are contemplated as well, including but not limited to oligonucleotide analogs and mimetics such as those described herein.

The antisense compounds preferably comprise from about 8 to about 80 nucleobases (i.e. from about 8 to about 80 linked nucleosides. Compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length are also contemplated.

In one preferred embodiment, the antisense compounds are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the antisense compounds are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 8–80 nucleobases in length comprising a stretch of at least eight (8) consecutive nucleobases selected from within the illustrative antisense compounds are considered to be suitable antisense compounds as well.

Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). It is also understood that preferred antisense compounds may be represented by oligonucleotide sequences that comprise at least 8 consecutive nucleobases from an internal portion of the sequence of an illustrative preferred antisense compound, and may extend in either or both directions until the oligonucleotide contains about 8 to about 80 nucleobases.

One having skill in the art armed with the preferred antisense compounds illustrated herein will be able, without undue experimentation, to identify further preferred antisense compounds.

C. Oligonucleotide Targets

"Targeting" an antisense compound to a particular nucleic acid molecule can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. As described herein, the target nucleic acid encodes STAT5.

The targeting process usually also includes determination of at least one target region, segment, or site within the target nucleic acid for the antisense interaction to occur such that the desired effect, e.g., modulation of expression, will result. As used herein, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used herein, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. As used herein, "start codon" and "translation initiation codon" refer to the codon or codons that are used in vivo to initiate translation of an mRNA transcribed from a gene encoding STAT5, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds described herein.

The open reading frame (ORF) or "coding region," which is known in the art to refer to the region between the translation initiation codon and the translation termination codon, is also a region which may be targeted effectively. A preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. The types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve only to illustrate and describe particular embodiments. Additional preferred target segments may be identified by one having ordinary skill.

Target segments 8–80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). It is also understood that preferred antisense target segments may be represented by DNA or RNA sequences that comprise at least 8 consecutive nucleobases from an internal portion of the sequence of an illustrative preferred target segment, and may extend in either or both directions until the oligonucleotide contains about 8 to about 80 nucleobases. One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

The oligomeric antisense compounds may also be targeted to regions of the STAT5A target nucleobase sequence (e.g., such as those disclosed in Example 13) comprising nucleobases 1–80, 81–160, 161–240, 241–320, 321–400, 401–480, 481–560, 561–640, 641–720, 721–800, 801–880, 881–960, 961–1040, 1041–1120, 1121–1200, 1201–1280, 1281–1360, 1361–1440, 1441–1520, 1521–1600, 1601–1680, 1681–1760, 1761–1840, 1841–1920, 1921–2000, 2001–2080, 2081–2160, 2161–2240, 2241–2320, 2321–2400, 2401–2480, 2481–2560, 2561–2640, 2641–2720, 2721–2800, 2801–2880, 2881–2960, 2961–3040, 3041–3120, 3121–3200, 3201–3280, 3281–3360, 3361–3440, 3441–3520, 3521–3600, 3601–3680, 3681–3760, 3761–3840, 3841–3920, 3921–4000, 4001–4080, 4081–4160, 4161–4240, 4241–4298, or any combination thereof. The oligomeric antisense compounds may further be targeted to regions of the STAT5B target nucleobase sequence (e.g., such as those disclosed in Example 15) comprising nucleobases 1–80, 81–160, 161–240, 241–320, 321–400, 401–480, 481–560, 561–640, 641–720, 721–800, 801–880, 881–960, 961–1040, 1041–1120, 1121–1200, 1201–1280, 1281–1360, 1361–1440, 1441–1520, 1521–1600, 1601–1680, 1681–1760, 1761–1840, 1841–1920, 1921–2000, 2001–2080, 2081–2160, 2161–2240, 2241–2320, 2321–2400, 2401–2480, 2481–2560, 2561–2640, 2641–2716, or any combination thereof.

D. Screening and Target Validation

In a further embodiment, the "preferred target segments" identified herein may be employed in a screen for additional compounds that modulate the expression of STAT5. "Modulators" are those compounds that decrease or increase the expression of a nucleic acid molecule encoding STAT5 and which comprise at least an 8-nucleobase portion which is complementary to a preferred target segment. The screening method comprises the steps of contacting a preferred target segment of a nucleic acid molecule encoding STAT5 with one or more candidate modulators, and selecting for one or more candidate modulators which decrease or increase the expression of a nucleic acid molecule encoding STAT5. Once it is shown that the candidate modulator or modulators are capable of modulating (e.g. either decreasing or increasing) the expression of a nucleic acid molecule encoding STAT5, the modulator may then be employed in further investigative studies of the function of STAT5, or for use as a research, diagnostic, or therapeutic agent.

The preferred target segments may be also be combined with their respective complementary antisense compounds to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806–811; Timmons and Fire, *Nature* 1998, 395, 854; Timmons et at., *Gene*, 2001, 263, 103–112; Tabara et al., *Science*, 1998, 282, 430–431; Montgomery et al., *Proc. Natl. Acad. Sci. USA*, 1998, 95, 15502–15507; Tuschl et al., *Genes Dev.*, 1999, 13, 3191–3197; Elbashir et al., *Nature*, 2001, 411, 494–498; Elbashir et al., *Genes Dev.* 2001, 15, 188–200). For example, such double-stranded moieties have been shown to inhibit the target by the classical hybridization of antisense strand of the duplex to the target, thereby triggering enzymatic degradation of the target (Tijsterman et al., *Science*, 2002, 295, 694–697).

The antisense compounds can also be applied in the areas of drug discovery and target validation. The use of the compounds and preferred target segments identified herein in drug discovery efforts to elucidate relationships that exist between STAT5 and a disease state, phenotype, or condition is also contemplated. These methods include detecting or modulating STAT5 comprising contacting a sample, tissue, cell, or organism with the compounds described herein, measuring the nucleic acid or protein level of STAT5 and/or a related phenotypic or chemical endpoint at some time after treatment, and optionally comparing the measured value to a non-treated sample or sample treated with a further compound. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The antisense compounds can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds described herein, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U.S.A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J.*

*Cancer,* 1999, 35, 1895–904) and mass spectrometry methods (To, *Comb. Chem. High Throughput Screen,* 2000, 3, 235–41).

The antisense compounds described herein are useful for research and diagnostics, because these compounds hybridize to nucleic acids encoding STAT5. For example, oligonucleotides that are shown to hybridize with such efficiency and under such conditions as disclosed herein as to be effective STAT5 inhibitors will also be effective primers or probes under conditions favoring gene amplification or detection, respectively. These primers and probes are useful in methods requiring the specific detection of nucleic acid molecules encoding STAT5 and in the amplification of said nucleic acid molecules for detection or for use in further studies of STAT5. Hybridization of the antisense oligonucleotides, particularly the primers and probes described herein, with a nucleic acid encoding STAT5 can be detected by means known in the art. Such means may include conjugation of an enzyme to the oligonucleotide, radiolabelling of the oligonucleotide or any other suitable detection means. Kits using such detection means for detecting the level of STAT5 in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of STAT5 is treated by administering antisense compounds described herein. For example, in one non-limiting embodiment, the methods comprise the step of administering to the animal in need of treatment, a therapeutically effective amount of a STAT5 inhibitor. The STAT5 inhibitors effectively inhibit the activity of the STAT5 protein or inhibit the expression of the STAT5 protein. In one embodiment, the activity or expression of STAT5 in an animal is inhibited by about 10%. Preferably, the activity or expression of STAT5 in an animal is inhibited by about 30%. More preferably, the activity or expression of STAT5 in an animal is inhibited by 50% or more. Thus, the oligomeric antisense compounds modulate expression of STAT5 mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of STAT5 may be measured in serum, adipose tissue, liver or any other body fluid, tissue or organ of the animal. Preferably, the cells contained within said fluids, tissues or organs being analyzed contain a nucleic acid molecule encoding STAT5 protein and/or the STAT5 protein itself.

The antisense compounds are utilized in pharmaceutical compositions by adding an effective amount of a compound to a suitable pharmaceutically acceptable diluent or carrier. The compounds and methods described herein are also useful prophylactically.

F. Modifications

As is known in the art, a nucleoside is a base-sugar combination. The base portion of the nucleoside is normally a heterocyclic base sometimes referred to as a "nucleobase" or simply a "base". The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds include oligonucleotides containing modified backbones or non-natural-internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriaminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'–5' linkages, 2'–5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred antisense compounds, e.g., oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497–1500.

Some embodiments are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified antisense compounds may also contain one or more substituted sugar moieties. Preferred are antisense compounds, preferably antisense oligonucleotides, comprising one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylamino-ethoxyethoxy (also known in the art as 2'-O-dimethylamino-ethoxy-ethyl or 2'-DMAEOE), i.e., 2'-O—$CH_2$—O—$CH_2$—N($CH_3$)$_2$, also described in examples hereinbelow.

Other preferred modifications include 2'-methoxy (2'-O—$CH_3$), 2'-aminopropoxy (2'-OCH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'–5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in WO 98/39352 and WO 99/14226.

Natural and Modified Nucleobases

Antisense compounds may also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the compounds described herein. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121; 5,596,091; 5,614,617; 5,645,985; 5,830,653; 5,763, 588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the antisense compounds involves chemically linking to the antisense compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of the compounds described herein. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Antisense compounds may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

Other embodiments also include antisense compounds which are chimeric compounds. "Chimeric" antisense compounds or "chimeras" are antisense compounds, particularly oligonucleotides, which contain two or more chemically distinct regions, each made up of at least one monomer unit, i.e., a nucleotide in the case of an oligonucleotide compound. Chimeric antisense oligonucleotides are thus a form of antisense compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds described herein may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds described herein: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

Another embodiment is pharmaceutical compositions and formulations which include the antisense compounds described herein. The pharmaceutical compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions may be formulated into any of many possible dosage forms such as, but not limited to, tablets, capsules, gel capsules, liquid syrups, soft gels, suppositories, and enemas. The compositions may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions include, but are not limited to, solutions, emulsions, foams and liposome-containing formulations. The pharmaceutical compositions and formulations may comprise one or more penetration enhancers, carriers, excipients or other active or inactive ingredients.

Emulsions are typically heterogenous systems of one liquid dispersed in another in the form of droplets usually exceeding 0.1 µm in diameter. Emulsions may contain additional components in addition to the dispersed phases, and the active drug which may be present as a solution in either the aqueous phase, oily phase or itself as a separate phase. Microemulsions are also contemplated. Emulsions and their uses are well known in the art and are further described in U.S. Pat. No. 6,287,860, which is incorporated herein in its entirety.

Formulations include liposomal formulations. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and non-cationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions may also include surfactants. The use of surfactants in drug products, formulations and in emulsions is well known in the art. Surfactants and their uses are further described in U.S. Pat. No. 6,287,860, which is incorporated herein in its entirety.

In one embodiment, various penetration enhancers are employed to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. applications Ser. No. 09/108,673 (filed Jul. 1, 1998), Ser. No. 09/315,298 (filed May 20, 1999) and Ser. No. 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the antisense compounds described herein, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions described herein. Combinations of antisense compounds and other non-antisense drugs are also contemplated. Two or more combined compounds may be used together or sequentially.

In another related embodiment, the compositions may contain one or more antisense compounds, particularly oligonucleotides, targeted to a first nucleic acid and one or more additional antisense compounds targeted to a second nucleic acid target. Alternatively, compositions may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

While preferred embodiments have been discussed herein, the following examples are meant to be illustrative and not limiting. Each of the references, GenBank accession numbers, and the like recited in the present application is incorporated herein by reference in its entirety.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylamino-oxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine 5'-O-tert-butyldiphenylsilyl-2'-O-[(2-formadoximinooxy)ethyl]-5-methyluridine, 5'-O-tert-Butyldiphenylsilyl-2'-O-[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite.

Example 2

Oligonucleotide and Oligonucleoside Synthesis

The antisense compounds described herein may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12–16 hr), the oligonucleotides were recovered by precipitating with >3 volumes of ethanol from a 1 M NH$_4$OAc solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820–11821; Matteucci, M. D. and Caruthers, M. H. *J. Am. Chem. Soc.*, 1981, 103, 3185–3191; Beaucage, S. L. and Caruthers, M. H. *Tetrahedron Lett.*, 1981, 22, 1859–1862; Dahl, B. J., et al., *Acta Chem. Scand.*, 1990, 44, 639–641; Reddy, M. P., et al., *Tetrahedron Lett.*, 1994, 25, 4311–4314; Wincott, F. et al., *Nucleic Acids Res.*, 1995, 23, 2677–2684; Griffin, B. E., et al., *Tetrahedron*, 1967, 23, 2301–2313; Griffin, B. E., et al., *Tetrahedron*, 1967, 23, 2315–2331).

RNA antisense compounds (RNA oligonucleotides) can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 µl of each of the complementary strands of RNA oligonucleotides (50 µM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid, or for diagnostic or therapeutic purposes.

Example 4

Synthesis of Chimeric Compounds

Chimeric oligonucleotides, oligonucleosides or mixed oligonucleotides/oligonucleosides can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]--[2'-deoxy]--[2'-O—Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH$_4$OH) for 12–16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]--[2'-deoxy]--[2'-O-(Methoxyethyl)] Chimeric Phosphorothioate Oligonucleotides

[2'-O-(2-methoxyethyl)]--[2'-deoxy]--[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]--[2'-deoxy Phosphorothioate]--[2'-O-(2-Methoxyethyl) Phosphodiester] Chimeric Oligonucleotides

[2'-O-(2-methoxyethyl phosphodiester]--[2'-deoxy phosphorothioate]--[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting STAT5

A series of nucleic acid duplexes comprising the antisense compounds described herein and their complements can be designed to target STAT5. The nucleobase sequence of the antisense strand of the duplex comprises at least an 8-nucleobase portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 214) and having a two-nucleobase overhang of deoxythymidine(dT) would have the following structure:

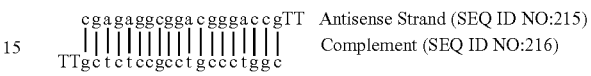
Antisense Strand (SEQ ID NO:215)
Complement (SEQ ID NO:216)

In another embodiment, a duplex comprising an antisense strand having the same sequence CGAGAGGCGGACGG-GACCG (SEQ ID NO: 214) maybe prepared with blunt ends (no single stranded overhang) as shown:

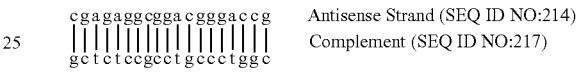
Antisense Strand (SEQ ID NO:214)
Complement (SEQ ID NO:217)

RNA strands of the duplex can be synthesized by methods disclosed herein or purchased from Dharmacon Research Inc., (Lafayette, Colo.). Once synthesized, the complementary strands are annealed. The single strands are aliquotted and diluted to a concentration of 50 μM. Once diluted, 30 μL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 μL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 μM. This solution can be stored frozen (−20° C.) and freeze-thawed up to 5 times.

Once prepared, the duplexed antisense compounds are evaluated for their ability to modulate STAT5 expression.

When cells reached 80% confluency, they are treated with duplexed antisense compounds. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12–16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Treatment With Antisense Compounds:

When cells reached 65–75% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligonucleotide. Cells are treated and data are obtained in triplicate. After 4–7 hours of treatment at 37° C., the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGT-CATCGCTCCTCAGGG, SEQ ID NO: 1) which is targeted to human H-ras, or ISIS 18078, (GTGCGCGCGAGC-CCGAAATC, SEQ ID NO: 2) which is targeted to human Jun-N-terminal kinase-2 (JNK2). Both controls are 2′-O- methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of STAT5 Expression

Antisense modulation of STAT5 expression can be assayed in a variety of ways known in the art. For example, STAT5 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. The preferred method of RNA analysis is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of STAT5 can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to STAT5 can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays for the Use of STAT5 Inhibitors

Phenotypic Assays

Once STAT5 inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of STAT5 in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with STAT5 inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the STAT5 inhibitors. Hallmark genes, or those genes suspected to be associated with a specific disease state, condition, or phenotype, are measured in both treated and untreated cells.

Example 12

RNA Isolation

Poly(A)+mRNA Isolation

Poly(A)+mRNA was isolated according to Miura et al., (*Clin. Chem.*, 1996, 42, 1758–1764). Other methods for poly(A)+mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 μL cold PBS. 150 μL Buffer RLT was added to each well and the plate vigorously agitated for 20 seconds. 150 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 μL of Buffer RW1 was added to each well of the RNEASY 96™ plate and incubated for 15 minutes and the vacuum was again applied for 1 minute. An additional 500 μL of Buffer RW1 was added to each well of the RNEASY $_{96}$™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of STAT5 mRNA Levels

Quantitation of STAT5 mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISMS Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 μL PCR cocktail (2.5×PCR buffer minus MgCl$_2$, 6.6 MM MgCl$_2$, 375 μM each of DATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 μL total RNA solution (20–200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368–374).

In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Probes and primers to human STAT5A were designed to hybridize to a human STAT5A sequence, using published sequence information (GenBank accession number NM_003152.2, incorporated herein as SEQ ID NO: 4). For human STAT5A the PCR primers were:
forward primer: AGAGTGCGCCGAGTCTGTCT (SEQ ID NO: 5) reverse primer: GCATTGAGTGCCTGCAGTGA (SEQ ID NO: 6) and the PCR probe was: FAM-TGT- CATGGTAGAGACCGAGCCTCT-TAMRA (SEQ ID NO: 7) where FAM is the fluorescent dye and TAMRA is the quencher dye.

For human GAPDH the PCR primers were:
forward primer: GAAGGTGAAGGTCGGAGTC(SEQ ID NO: 8) reverse primer: GAAGATGGTGATGGGATTTC (SEQ ID NO: 9) and the PCR probe was: 5' JOE-CAAGCTTCCCGTTCTCAGCC-TAMRA 3' (SEQ ID NO: 10) where JOE is the fluorescent reporter dye and TAMRA is the quencher dye.

Example 14

Northern Blot Analysis of STAT5 mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human STAT5A, a human STAT5A specific probe was prepared by PCR using the forward primer AGAGTGCGCCGAGTCTGTCT (SEQ ID NO: 5) and the reverse primer GCATTGAGTGCCTGCAGTGA (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human STAT5A Expression by Chimeric Phosphorothioate Oligonucleotides Having 2'-MOE Wings and a Deoxy Gap A series of antisense compounds was designed to target different regions of the human STAT5A RNA, using published sequences for human STAT5A (GenBank accession number NM_003152.2, incorporated herein as SEQ ID NO: 4). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on STAT5A mRNA levels by transfection and quantitative real-time PCR as described in other examples herein. Data are averages from two experiments in which T-24 cells were treated with 150 nM of the antisense oligonucleotides. The positive control for each datapoint is identified in the table by sequence ID number. If present, "N.D." indicates "no data".

TABLE 1

Inhibition of human STAT5A mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 130817 | Coding | 4 | 1173 | gcttggatcctcaggctctc | 16 | 12 | 1 |
| 130818 | Coding | 4 | 1244 | gcttctgctggagggccgtc | 43 | 13 | 1 |
| 130820 | Coding | 4 | 1361 | tgatggtctgctgcttccgc | 75 | 14 | 1 |
| 130821 | Coding | 4 | 1559 | gcatctcctccactgggccg | 64 | 15 | 1 |
| 130824 | Coding | 4 | 1676 | cggtggctgcaaacttggtc | 78 | 16 | 1 |
| 130825 | Coding | 4 | 2117 | gcacggcaaatggcaccctg | 44 | 17 | 1 |
| 130826 | Coding | 4 | 2795 | gggcctggtccatgtacgtg | 36 | 18 | 1 |
| 153814 | 3'UTR | 4 | 3681 | gagcagctcagaaaccctca | 73 | 19 | 1 |
| 153820 | 3'UTR | 4 | 3895 | accaaccctccaagtcccgg | 77 | 20 | 1 |
| 315651 | Coding | 4 | 810 | ccctccaggagctgggtggc | 57 | 21 | 1 |
| 315652 | Coding | 4 | 820 | ctgcaccaggccctccagga | 80 | 22 | 1 |
| 315653 | Coding | 4 | 828 | tgcagctcctgcaccaggcc | 82 | 23 | 1 |

TABLE 1-continued

Inhibition of human STAT5A mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 315654 | Coding | 4 | 837 | gccttcttctgcagctcctg | 75 | 24 | 1 |
| 315655 | Coding | 4 | 859 | atcttccccacctggtgct | 56 | 25 | 1 |
| 315656 | Coding | 4 | 869 | gtaaaaacccatcttcccc | 51 | 26 | 1 |
| 315657 | Coding | 4 | 874 | cttcagtaaaaacccatctt | 42 | 27 | 1 |
| 315658 | Coding | 4 | 884 | ccagcttgatcttcagtaaa | 66 | 28 | 1 |
| 315659 | Coding | 4 | 891 | tagtgccccagcttgatctt | 66 | 29 | 1 |
| 315660 | Coding | 4 | 951 | cggatgcagcggaccagctc | 57 | 30 | 1 |
| 315661 | Coding | 4 | 997 | attgttggcttctcggacca | 67 | 31 | 1 |
| 315662 | Coding | 4 | 1083 | accagtcgcagctcctcaaa | 55 | 32 | 1 |
| 315663 | Coding | 4 | 1092 | tcctgcgtgaccagtcgcag | 78 | 33 | 1 |
| 315664 | Coding | 4 | 1100 | tctctgtgtcctgcgtgacc | 87 | 34 | 1 |
| 315665 | Coding | 4 | 1105 | ctcattctctgtgtcctgcg | 79 | 35 | 1 |
| 315666 | Coding | 4 | 1134 | tactcctgagtctgctgcag | 88 | 36 | 1 |
| 315667 | Coding | 4 | 1149 | tactggatgatgaagtactc | 63 | 37 | 1 |
| 315668 | Coding | 4 | 1164 | ctcaggctctcctggtactg | 58 | 38 | 1 |
| 315670 | Coding | 4 | 1181 | caaactgagcttggatcctc | 71 | 39 | 1 |
| 315671 | Coding | 4 | 1231 | ggccgtctcccggctcagac | 38 | 40 | 1 |
| 315672 | Coding | 4 | 1236 | tggagggccgtctcccggct | 83 | 41 | 1 |
| 315674 | Coding | 4 | 1256 | ccagagacacctgcttctgc | 68 | 42 | 1 |
| 315675 | Coding | 4 | 1266 | aaccaggcctccagagacac | 69 | 43 | 1 |
| 315676 | Coding | 4 | 1271 | gctgcaaccaggcctccaga | 74 | 44 | 1 |
| 315677 | Coding | 4 | 1281 | tgtgcctcacgctgcaacca | 80 | 45 | 1 |
| 315678 | Coding | 4 | 1291 | ctgcagtgtctgtgcctcac | 68 | 46 | 1 |
| 315679 | Coding | 4 | 1301 | cgcggtactgctgcagtgtc | 72 | 47 | 1 |
| 315680 | Coding | 4 | 1319 | gcttctcggccagctccacg | 74 | 48 | 1 |
| 315681 | Coding | 4 | 1324 | ctggtgcttctcggccagct | 80 | 49 | 1 |
| 315682 | Coding | 4 | 1332 | agggtcttctggtgcttctc | 0 | 50 | 1 |
| 315683 | Coding | 4 | 1337 | gctgcagggtcttctggtgc | 46 | 51 | 1 |
| 315684 | Coding | 4 | 1347 | ttccgcagcagctgcagggt | 43 | 52 | 1 |
| 315686 | Coding | 4 | 1367 | ccaggatgatggtctgctgc | 70 | 53 | 1 |
| 315687 | Coding | 4 | 1373 | cgtcatccaggatgatggtc | 56 | 54 | 1 |
| 315688 | Coding | 4 | 1391 | gcttccactggatcagctcg | 66 | 55 | 1 |
| 315689 | Coding | 4 | 1401 | tgctgccgccgcttccactg | 82 | 56 | 1 |
| 315690 | Coding | 4 | 1443 | acgtccaggctgccctcggg | 72 | 57 | 1 |
| 315691 | Coding | 4 | 1455 | caggactgtagcacgtccag | 80 | 58 | 1 |

TABLE 1-continued

Inhibition of human STAT5A mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 315692 | Coding | 4 | 1465 | cttctcacaccaggactgta | 57 | 59 | 1 |
| 315693 | Coding | 4 | 1475 | tctcggccaacttctcacac | 62 | 60 | 1 |
| 315694 | Coding | 4 | 1485 | tgccagatgatctcggccaa | 69 | 61 | 1 |
| 315695 | Coding | 4 | 1495 | ctgccggttctgccagatga | 72 | 62 | 1 |
| 315696 | Coding | 4 | 1505 | tgcggatctgctgccggttc | 67 | 63 | 1 |
| 315697 | Coding | 4 | 1515 | tgctcagccctgcggatctg | 76 | 64 | 1 |
| 315698 | Coding | 4 | 1525 | ctggcagaggtgctcagccc | 75 | 65 | 1 |
| 315699 | Coding | 4 | 1536 | atgggcagctgctggcagag | 42 | 66 | 1 |
| 315701 | Coding | 4 | 1570 | gacctcggccagcatctcct | 50 | 67 | 1 |
| 315702 | Coding | 4 | 1591 | aatgtccgtgatggtggcgt | 74 | 68 | 1 |
| 315703 | Coding | 4 | 1600 | ggctgagataatgtccgtga | 70 | 69 | 1 |
| 315704 | Coding | 4 | 1610 | tggtcaccagggctgagata | 63 | 70 | 1 |
| 315705 | Coding | 4 | 1635 | ggctgcttctcaatgatgaa | 45 | 71 | 1 |
| 315706 | Coding | 4 | 1654 | ggtcttcaggacctgaggag | 73 | 72 | 1 |
| 315708 | Coding | 4 | 1741 | gatggtggccttcacctggg | 43 | 73 | 1 |
| 315709 | Coding | 4 | 1751 | gctcactgatgatggtggcc | 68 | 74 | 1 |
| 315710 | Coding | 4 | 1761 | ttggcctgctgctcactgat | 80 | 75 | 1 |
| 315711 | Coding | 4 | 1770 | agcagagacttggcctgctg | 77 | 76 | 1 |
| 315712 | Coding | 4 | 1848 | gtggcttggtggtactccat | 83 | 77 | 1 |
| 315714 | Coding | 4 | 2135 | gccacagcactttgtcaggc | 68 | 78 | 1 |
| 315715 | Coding | 4 | 2169 | ttgaatttcatgttgagcgc | 77 | 79 | 1 |
| 315716 | Coding | 4 | 2189 | ggttgctctgcacttcggcc | 43 | 80 | 1 |
| 315717 | Coding | 4 | 2209 | gttctccttggtcaggcccc | 66 | 81 | 1 |
| 315718 | Coding | 4 | 2229 | ttctgcgccaggaacacgag | 80 | 82 | 1 |
| 315719 | Coding | 4 | 2249 | tgctgctgttgttgaacagt | 74 | 83 | 1 |
| 315720 | Coding | 4 | 2269 | actgtagtcctccaggtggc | 43 | 84 | 1 |
| 315721 | Coding | 4 | 2277 | gacaggccactgtagtcctc | 35 | 85 | 1 |
| 315722 | Coding | 4 | 2703 | tatccatcaacagctttagc | 77 | 86 | 1 |
| 315723 | Coding | 4 | 2730 | accacttgcttgatctgtgg | 76 | 87 | 1 |
| 315724 | Coding | 4 | 2740 | aaactcagggaccacttgct | 80 | 88 | 1 |
| 315726 | Coding | 4 | 2843 | tctgtgggtacatgttatag | 79 | 89 | 1 |

As shown in Table 1, SEQ ID NOs 14, 15, 16, 19, 20, 21, 22, 23, 24, 25, 28, 29, 30, 31, 32, 33, 34, 35, 36, 37, 38, 39, 41, 42, 43, 44, 45, 46, 47, 48, 49, 53, 54, 55, 56, 57, 58, 59, 60, 61, 62, 63, 64, 65, 68, 69, 70, 72, 74, 75, 76, 77, 78, 79, 81, 82, 83, 86, 87, 88 and 89 demonstrated at least 55% inhibition of human STAT5A expression in this assay and are therefore preferred. More preferred are SEQ ID NOs 36, 34, 77 and 23. The target regions to which these preferred sequences are complementary are herein referred to as "preferred target segments" and are therefore preferred for targeting by compounds described herein. These preferred target segments are shown in Table 2. These sequences are shown to contain thymine (T) but one of skill in the art will appreciate that thymine (T) is generally replaced by uracil (U) in RNA sequences. The sequences represent the reverse complement of the preferred antisense compounds shown in Table 1. "Target site" indicates the first (5'-most) nucleotide number on the particular target nucleic acid to which the oligonucleotide binds. Also shown in Table 2 is the species in which each of the preferred target segments was found.

TABLE 2

Sequence and position of preferred target segments identified in STAT5A.

| SITE ID | TARGET SEQ ID NO | TARGET SITE | SEQUENCE | REV COMP OF SEQ ID | ACTIVE IN | SEQ ID NO |
|---|---|---|---|---|---|---|
| 42321 | 4 | 1361 | gcggaagcagcagaccatca | 14 | H. sapiens | 90 |
| 42322 | 4 | 1559 | cggcccagtggaggagatgc | 15 | H. sapiens | 91 |
| 42325 | 4 | 1676 | gaccaagtttgcagccaccg | 16 | H. sapiens | 92 |
| 69127 | 4 | 3681 | tgagggtttctgagctgctc | 19 | H. sapiens | 93 |
| 69133 | 4 | 3895 | ccgggacttggagggttggt | 20 | H. sapiens | 94 |
| 231948 | 4 | 810 | gccacccagctcctggaggg | 21 | H. sapiens | 95 |
| 231949 | 4 | 820 | tcctggagggcctggtgcag | 22 | H. sapiens | 96 |
| 231950 | 4 | 828 | ggcctggtgcaggagctgca | 23 | H. sapiens | 97 |
| 231951 | 4 | 837 | caggagctgcagaagaaggc | 24 | H. sapiens | 98 |
| 231952 | 4 | 859 | agcaccaggtgggggaagat | 25 | H. sapiens | 99 |
| 231955 | 4 | 884 | tttactgaagatcaagctgg | 28 | H. sapiens | 100 |
| 231956 | 4 | 891 | aagatcaagctggggcacta | 29 | H. sapiens | 101 |
| 231957 | 4 | 951 | gagctggtccgctgcatccg | 30 | H. sapiens | 102 |
| 231958 | 4 | 997 | tggtccgagaagccaacaat | 31 | H. sapiens | 103 |
| 231959 | 4 | 1083 | tttgaggagctgcgactggt | 32 | H. sapiens | 104 |
| 231960 | 4 | 1092 | ctgcgactggtcacgcagga | 33 | H. sapiens | 105 |
| 231961 | 4 | 1100 | ggtcacgcaggacacagaga | 34 | H. sapiens | 106 |
| 231962 | 4 | 1105 | cgcaggacacagagaatgag | 35 | H. sapiens | 107 |
| 231963 | 4 | 1134 | ctgcagcagactcaggagta | 36 | H. sapiens | 108 |
| 231964 | 4 | 1149 | gagtacttcatcatccagta | 37 | H. sapiens | 109 |
| 231965 | 4 | 1164 | cagtaccaggagagcctgag | 38 | H. sapiens | 110 |
| 231967 | 4 | 1181 | gaggatccaagctcagtttg | 39 | H. sapiens | 111 |
| 231969 | 4 | 1236 | agccgggagacggccctcca | 41 | H. sapiens | 112 |
| 231971 | 4 | 1256 | gcagaagcaggtgtctctgg | 42 | H. sapiens | 113 |
| 231972 | 4 | 1266 | gtgtctctggaggcctggtt | 43 | H. sapiens | 114 |
| 231973 | 4 | 1271 | tctggaggcctggttgcagc | 44 | H. sapiens | 115 |
| 231974 | 4 | 1281 | tggttgcagcgtgaggcaca | 45 | H. sapiens | 116 |
| 231975 | 4 | 1291 | gtgaggcacagacactgcag | 46 | H. sapiens | 117 |
| 231976 | 4 | 1301 | gacactgcagcagtaccgcg | 47 | H. sapiens | 118 |
| 231977 | 4 | 1319 | cgtggagctggccgagaagc | 48 | H. sapiens | 119 |
| 231978 | 4 | 1324 | agctggccgagaagcaccag | 49 | H. sapiens | 120 |
| 231983 | 4 | 1367 | gcagcagaccatcatcctgg | 53 | H. sapiens | 121 |
| 231984 | 4 | 1373 | gaccatcatcctggatgacg | 54 | H. sapiens | 122 |

TABLE 2-continued

Sequence and position of preferred target segments identified in STAT5A.

| SITE ID | TARGET SEQ ID NO | TARGET SITE | SEQUENCE | REV COMP OF SEQ ID | ACTIVE IN | SEQ ID NO |
|---|---|---|---|---|---|---|
| 231985 | 4 | 1391 | cgagctgatccagtggaagc | 55 | H. sapiens | 123 |
| 231986 | 4 | 1401 | cagtggaagcggcggcagca | 56 | H. sapiens | 124 |
| 231987 | 4 | 1443 | cccgagggcagcctggacgt | 57 | H. sapiens | 125 |
| 231988 | 4 | 1455 | ctggacgtgctacagtcctg | 58 | H. sapiens | 126 |
| 231989 | 4 | 1465 | tacagtcctggtgtgagaag | 59 | H. sapiens | 127 |
| 231990 | 4 | 1475 | gtgtgagaagttggccgaga | 60 | H. sapiens | 128 |
| 231991 | 4 | 1485 | ttggccgagatcatctggca | 61 | H. sapiens | 129 |
| 231992 | 4 | 1495 | tcatctggcagaaccggcag | 62 | H. sapiens | 130 |
| 231993 | 4 | 1505 | gaaccggcagcagatccgca | 63 | H. sapiens | 131 |
| 231994 | 4 | 1515 | cagatccgcagggctgagca | 64 | H. sapiens | 132 |
| 231998 | 4 | 1525 | gggctgagcacctctgccag | 65 | H. sapiens | 133 |
| 231999 | 4 | 1591 | acgccaccatcacggacatt | 68 | H. sapiens | 134 |
| 232000 | 4 | 1600 | tcacggacattatctcagcc | 69 | H. sapiens | 135 |
| 232001 | 4 | 1610 | tatctcagccctggtgacca | 70 | H. sapiens | 136 |
| 232003 | 4 | 1654 | ctcctcaggtcctgaagacc | 72 | H. sapiens | 137 |
| 232006 | 4 | 1751 | ggccaccatcatcagtgagc | 74 | H. sapiens | 138 |
| 232007 | 4 | 1761 | atcagtgagcagcaggccaa | 75 | H. sapiens | 139 |
| 232008 | 4 | 1770 | cagcaggccaagtctctgct | 76 | H. sapiens | 140 |
| 232009 | 4 | 1848 | atggagtaccaccaagccac | 77 | H. sapiens | 141 |
| 232011 | 4 | 2135 | gcctgacaaagtgctgtggc | 78 | H. sapiens | 142 |
| 232012 | 4 | 2169 | gcgctcaacatgaaattcaa | 79 | H. sapiens | 143 |
| 232014 | 4 | 2209 | ggggcctgaccaaggagaac | 81 | H. sapiens | 144 |
| 232015 | 4 | 2229 | ctcgtgttcctggcgcagaa | 82 | H. sapiens | 145 |
| 232016 | 4 | 2249 | actgttcaacaacagcagca | 83 | H. sapiens | 146 |
| 232019 | 4 | 2703 | gctaaagctgttgatggata | 86 | H. sapiens | 147 |
| 232020 | 4 | 2730 | ccacagatcaagcaagtggt | 87 | H. sapiens | 148 |
| 232021 | 4 | 2740 | agcaagtggtccctgagttt | 88 | H. sapiens | 149 |
| 232023 | 4 | 2843 | ctataacatgtacccacaga | 89 | H. sapiens | 150 |

As these "preferred target segments" have been found by experimentation to be open to, and accessible for, hybridization with the antisense compounds described herein, one of skill in the art will recognize or be able to ascertain, using no more than routine experimentation, further embodiments that encompass other compounds that specifically hybridize to these preferred target segments and consequently inhibit the expression of STAT5.

Antisense compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

The compounds described in Table 1 also target the human STAT5B isoform. In a further embodiment, the compounds were analyzed for their effect on STAT5B mRNA levels by quantitative real-time PCR as described in other examples herein. Probes and primers to human STAT5B were designed to hybridize to a human STAT5B sequence, using published sequence information (GenBank accession number U48730.2, incorporated herein as SEQ ID NO: 151). For human STAT5B the PCR primers were:

forward primer: CTTCATCTTCACCAGAGGAATCACT (SEQ ID NO: 152) reverse primer: CTTCACATTATGAGTATTGTTTCAAAAGAG (SEQ ID NO: 153) and the PCR probe was: FAM-TGTGGATGTTTTAATTC-CATGAATC-TAMRA SEQ ID NO: 154) where FAM is the fluorescent dye and TAMRA is the quencher dye. Data are averages from two experiments in which T-24 cells were treated with 100 nM of the antisense oligonucleotides described herein. The positive control for each datapoint is identified in the table by sequence ID number. If present, "N.D." indicates "no data". If present, "–" indicates that no target site for a particular antisense compound is found in the referenced target sequence.

TABLE 3

Inhibition of human STAT5B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 130817 | Coding | 151 | 543 | gcttggatcctcaggctctc | 76 | 12 | 1 |
| 130818 | Coding | 151 | 614 | gcttctgctggagggccgtc | 76 | 13 | 1 |
| 130820 | Coding | 151 | 731 | tgatggtctgctgcttccgc | 66 | 14 | 1 |
| 130821 | Coding | 151 | 929 | gcatctcctccactgggccg | 53 | 15 | 1 |
| 130824 | Coding | – | – | cggtggctgcaaacttggtc | 86 | 16 | 1 |
| 130825 | Coding | 151 | 1487 | gcacggcaaatggcaccctg | 84 | 17 | 1 |
| 130826 | Coding | 151 | 2180 | gggcctggtccatgtacgtg | 69 | 18 | 1 |
| 153814 | 3'UTR | – | – | gagcagctcagaaaccctca | 3 | 19 | 1 |
| 153820 | 3'UTR | – | – | accaaccctccaagtcccgg | 8 | 20 | 1 |
| 315651 | Coding | 151 | 180 | ccctccaggagctgggtggc | 65 | 21 | 1 |
| 315652 | Coding | 151 | 190 | ctgcaccaggccctccagga | 89 | 22 | 1 |
| 315653 | Coding | 151 | 198 | tgcagctcctgcaccaggcc | 89 | 23 | 1 |
| 315654 | Coding | 151 | 207 | gccttcttctgcagctcctg | 87 | 24 | 1 |
| 315655 | Coding | 151 | 229 | atcttcccccacctggtgct | 45 | 25 | 1 |
| 315656 | Coding | 151 | 239 | gtaaaaacccatcttccccc | 49 | 26 | 1 |
| 315657 | Coding | 151 | 244 | cttcagtaaaaacccatctt | 39 | 27 | 1 |
| 315658 | Coding | 151 | 254 | ccagcttgatcttcagtaaa | 59 | 28 | 1 |
| 315659 | Coding | 151 | 261 | tagtgccccagcttgatctt | 43 | 29 | 1 |
| 315660 | Coding | 151 | 321 | cggatgcagcggaccagctc | 82 | 30 | 1 |
| 315661 | Coding | 151 | 367 | attgttggcttctcggacca | 63 | 31 | 1 |
| 315662 | Coding | 151 | 453 | accagtcgcagctcctcaaa | 64 | 32 | 1 |
| 315663 | Coding | 151 | 462 | tcctgcgtgaccagtcgcag | 80 | 33 | 1 |
| 315664 | Coding | 151 | 470 | tctctgtgtcctgcgtgacc | 86 | 34 | 1 |
| 315665 | Coding | 151 | 475 | ctcattctctgtgtcctgcg | 82 | 35 | 1 |
| 315666 | Coding | 151 | 504 | tactcctgagtctgctgcag | 88 | 36 | 1 |
| 315667 | Coding | 151 | 519 | tactggatgatgaagtactc | 67 | 37 | 1 |
| 315668 | Coding | 151 | 534 | ctcaggctctcctggtactg | 50 | 38 | 1 |
| 315670 | Coding | 151 | 551 | caaactgagcttggatcctc | 65 | 39 | 1 |
| 315671 | Coding | 151 | 601 | ggccgtctcccggctcagac | 75 | 40 | 1 |
| 315672 | Coding | 151 | 606 | tggagggccgtctcccggct | 88 | 41 | 1 |
| 315674 | Coding | 151 | 626 | ccagagacacctgcttctgc | 65 | 42 | 1 |

TABLE 3-continued

Inhibition of human STAT5B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 315675 | Coding | 151 | 636 | aaccaggcctccagagacac | 60 | 43 | 1 |
| 315676 | Coding | 151 | 641 | gctgcaaccaggcctccaga | 78 | 44 | 1 |
| 315677 | Coding | 151 | 651 | tgtgcctcacgctgcaacca | 81 | 45 | 1 |
| 315678 | Coding | 151 | 661 | ctgcagtgtctgtgcctcac | 80 | 46 | 1 |
| 315679 | Coding | 151 | 671 | cgcggtactgctgcagtgtc | 82 | 47 | 1 |
| 315680 | Coding | 151 | 689 | gcttctcggccagctccacg | 87 | 48 | 1 |
| 315681 | Coding | 151 | 694 | ctggtgcttctcggccagct | 90 | 49 | 1 |
| 315682 | Coding | 151 | 702 | agggtcttctggtgcttctc | 66 | 50 | 1 |
| 315683 | Coding | 151 | 707 | gctgcagggtcttctggtgc | 66 | 51 | 1 |
| 315684 | Coding | 151 | 717 | ttccgcagcagctgcagggt | 65 | 52 | 1 |
| 315686 | Coding | 151 | 737 | ccaggatgatggtctgctgc | 85 | 53 | 1 |
| 315687 | Coding | 151 | 743 | cgtcatccaggatgatggtc | 78 | 54 | 1 |
| 315688 | Coding | 151 | 761 | gcttccactggatcagctcg | 68 | 55 | 1 |
| 315689 | Coding | 151 | 771 | tgctgccgccgcttccactg | 86 | 56 | 1 |
| 315690 | Coding | 151 | 813 | acgtccaggctgccctcggg | 80 | 57 | 1 |
| 315691 | Coding | 151 | 825 | caggactgtagcacgtccag | 71 | 58 | 1 |
| 315692 | Coding | 151 | 835 | cttctcacaccaggactgta | 55 | 59 | 1 |
| 315693 | Coding | 151 | 845 | tctcggccaacttctcacac | 70 | 60 | 1 |
| 315694 | Coding | 151 | 855 | tgccagatgatctcggccaa | 86 | 61 | 1 |
| 315695 | Coding | 151 | 865 | ctgccggttctgccagatga | 83 | 62 | 1 |
| 315696 | Coding | 151 | 875 | tgcggatctgctgccggttc | 69 | 63 | 1 |
| 315697 | Coding | 151 | 885 | tgctcagccctgcggatctg | 84 | 64 | 1 |
| 315698 | Coding | 151 | 895 | ctggcagaggtgctcagccc | 76 | 65 | 1 |
| 315699 | Coding | 151 | 906 | atgggcagctgctggcagag | 60 | 66 | 1 |
| 315701 | Coding | 151 | 940 | gacctcggccagcatctcct | 59 | 67 | 1 |
| 315702 | Coding | 151 | 961 | aatgtccgtgatggtggcgt | 80 | 68 | 1 |
| 315703 | Coding | 151 | 970 | ggctgagataatgtccgtga | 71 | 69 | 1 |
| 315704 | Coding | 151 | 980 | tggtcaccagggctgagata | 79 | 70 | 1 |

TABLE 3-continued

Inhibition of human STAT5B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 315705 | Coding | 151 | 1005 | ggctgcttctcaatgatgaa | 60 | 71 | 1 |
| 315706 | Coding | 151 | 1024 | ggtcttcaggacctgaggag | 78 | 72 | 1 |
| 315708 | Coding | 151 | 1111 | gatggtggccttcacctggg | 67 | 73 | 1 |
| 315709 | Coding | 151 | 1121 | gctcactgatgatggtggcc | 82 | 74 | 1 |
| 315710 | Coding | 151 | 1131 | ttggcctgctgctcactgat | 0 | 75 | 1 |
| 315711 | Coding | 151 | 1140 | agcagagacttggcctgctg | 58 | 76 | 1 |
| 315712 | Coding | 151 | 1218 | gtggcttggtggtactccat | 90 | 77 | 1 |
| 315714 | Coding | 151 | 1505 | gccacagcactttgtcaggc | 84 | 78 | 1 |
| 315715 | Coding | 151 | 1539 | ttgaatttcatgttgagcgc | 79 | 79 | 1 |
| 315716 | Coding | 151 | 1559 | ggttgctctgcacttcggcc | 75 | 80 | 1 |
| 315717 | Coding | 151 | 1579 | gttctccttggtcaggcccc | 80 | 81 | 1 |
| 315718 | Coding | 151 | 1599 | ttctgcgccaggaacacgag | 85 | 82 | 1 |
| 315719 | Coding | 151 | 1619 | tgctgctgttgttgaacagt | 72 | 83 | 1 |
| 315720 | Coding | 151 | 1639 | actgtagtcctccaggtggc | 73 | 84 | 1 |
| 315721 | Coding | 151 | 1647 | gacaggccactgtagtcctc | 74 | 85 | 1 |
| 315722 | Coding | 151 | 2088 | tatccatcaacagctttagc | 68 | 86 | 1 |
| 315723 | Coding | 151 | 2115 | accacttgcttgatctgtgg | 79 | 87 | 1 |
| 315724 | Coding | 151 | 2125 | aaactcagggaccacttgct | 77 | 88 | 1 |
| 315726 | Coding | 151 | 2228 | tctgtgggtacatgttatag | 78 | 89 | 1 |

As shown in Table 3, SEQ ID NOs 12, 13, 14, 16, 17, 18, 21, 22, 23, 24, 30, 31, 32, 33, 34, 35, 36, 37, 39, 40, 41, 42, 43, 44, 45, 46, 47, 48, 49, 50, 51, 52, 53, 54, 55, 56, 57, 58, 60, 61, 62, 63, 64, 65, 66, 68, 69, 70, 71, 72, 73, 74, 77, 78, 79, 80, 81, 82, 83, 84, 85, 86, 87, 88 and 89, demonstrated at least 60% inhibition of human STAT5B expression in this assay and are therefore preferred. More preferred are SEQ ID NOs 77, 49, 22 and 23. In another embodiment, the antisense compounds disclosed herein optionally exclude ISIS 130826. The target regions to which these preferred sequences are complementary are herein referred to as "preferred target segments" and are therefore preferred for targeting by compounds described herein.

In another embodiment, a single antisense oligonucleotide is used to target and inhibit expression of nucleic acid encoding both STAT5A and STAT5B. For example, ISIS 315652 (SEQ ID NO: 22), 315653 (SEQ ID NO: 23), and 315715 (SEQ ID NO: 79) each result in similar inhibition of expression of both STAT5 isoforms (Tables 1 and 3). The use of any antisense compound targeted to STAT5 which inhibits expression of both STAT5 isoforms by at least about 10% is contemplated.

Example 16

Design of Chimeric Phosphorothioate Oligonucleotides Targeting Human STAT5 Having 2'-MOE Wings and a Deoxy Gap In a further embodiment, additional antisense compounds were designed to target different regions of the human STAT5 RNA, using published sequences for human STAT5A and human STAT5B (GenBank accession number NM_003152.2, incorporated herein as SEQ ID NO: 4; GenBank accession number U48730.2, incorporated herein as SEQ ID NO: 151). The compounds are shown in Table 4. "Target site" indicates the first (5'-most) nucleotide number on the particular target sequence to which the compound binds. The target site for each antisense compound with respect to STAT5A or STAT5B is indicated. All compounds in Table 4 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines.

TABLE 4

Chimeric phosphorothioate oligonucleotides targeting human STAT5 having 2'-MOE wings and a deoxy gap

| | | STAT5A | | STAT5B | | | |
|---|---|---|---|---|---|---|---|
| ISIS # | REGION | TARGET SEQ ID NO | TARGET SITE | TARGET SEQ ID NO | TARGET SITE | SEQUENCE | SEQ ID NO |
| 130819 | Coding | 4 | 1316 | 151 | 686 | tctcggccagctccacgcgg | 155 |
| 130822 | Coding | 4 | 1568 | 151 | 938 | cctcggccagcatctcctcc | 156 |
| 130823 | Coding | 4 | 1589 | 151 | 959 | tgtccgtgatggtggcgttg | 157 |
| 315669 | Coding | 4 | 1169 | 151 | 539 | ggatcctcaggctctcctgg | 158 |
| 315673 | Coding | 4 | 1251 | 151 | 621 | gacacctgcttctgctggag | 159 |
| 315685 | Coding | 4 | 1357 | 151 | 727 | ggtctgctgcttccgcagca | 160 |
| 315700 | Coding | 4 | 1558 | 151 | 928 | catctcctccactgggccgg | 161 |
| 315707 | Coding | 4 | 1668 | 151 | 1038 | gcaaacttggtctgggtctt | 162 |
| 315713 | Coding | 4 | 2115 | 151 | 1485 | acggcaaatggcaccctgcc | 163 |
| 315725 | Coding | 4 | 2792 | 151 | 2177 | cctggtccatgtacgtggcg | 164 |

Example 17

Design of Chimeric Phosphorothioate Oligonucleotides Targeting Human STAT5A Having 2'-MOE Wings and a Deoxy Gap In a further embodiment, additional antisense compounds were designed to target different regions of the human STAT5A RNA, using published sequences for human STAT5A (GenBank accession number NM_003152.2, incorporated herein as SEQ ID NO: 4). The compounds are shown in Table 5. "Target site" indicates the first (5'-most) nucleotide number on the particular target sequence to which the compound binds. All compounds in Table 5 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

TABLE 5

Chimeric phosphorothioate oligonucleotides targeting human STAT5A having 2'-MOE wings and a deoxy gap

| ISIS # | Region | TARGET SEQ ID NO | TARGET SITE | SEQUENCE | SEQ ID NO |
|---|---|---|---|---|---|
| 153802 | 3' UTR | 4 | 3057 | ccgcttcacattgcatattg | 165 |
| 153803 | 3' UTR | 4 | 3060 | cgaccgcttcacattgcata | 166 |
| 153804 | 3' UTR | 4 | 3148 | tgcacaaggacacacacaca | 167 |
| 153805 | 3' UTR | 4 | 3159 | ggcgtagctcatgcacaagg | 168 |
| 153806 | 3' UTR | 4 | 3189 | gccacatcccaggactgcac | 169 |
| 153807 | 3' UTR | 4 | 3281 | tgcagtgacagaggctcggt | 170 |
| 153808 | 3' UTR | 4 | 3311 | ggaggaataggtctggctgc | 171 |
| 153809 | 3' UTR | 4 | 3318 | gggcccaggaggaataggtc | 172 |
| 153810 | 3' UTR | 4 | 3420 | ggcaaagcttctcactccgg | 173 |
| 153811 | 3' UTR | 4 | 3616 | acgcgctctcatagggttca | 174 |
| 153812 | 3' UTR | 4 | 3640 | tgctaaggacatggccgggc | 175 |
| 153813 | 3' UTR | 4 | 3669 | aaccctcactcaaaccggcg | 176 |
| 153815 | 3' UTR | 4 | 3709 | gccaagcagccaagcaagga | 177 |
| 153816 | 3' UTR | 4 | 3750 | aaacgtgggcaacagcatca | 178 |
| 153817 | 3' UTR | 4 | 3807 | gagaggcaagcaaagaaggc | 179 |
| 153818 | 3' UTR | 4 | 3863 | cccaccatatcctagaccca | 180 |
| 153819 | 3' UTR | 4 | 3871 | cctgtccacccaccatatcc | 181 |
| 153821 | 3' UTR | 4 | 3907 | ggaggcaagaggaccaaccc | 182 |
| 153822 | 3' UTR | 4 | 3910 | ccaggaggcaagaggaccaa | 183 |
| 153823 | 3' UTR | 4 | 3985 | ccagattccacaggcacgca | 184 |
| 153824 | 3' UTR | 4 | 4023 | ccagcggagtcaaaccagat | 185 |
| 153825 | 3' UTR | 4 | 4081 | gcctcaccagaacacagcca | 186 |

TABLE 5-continued

Chimeric phosphorothioate oligonucleotides targeting human STAT5A having 2'-MOE wings and a deoxy gap

| ISIS # | Region | TARGET SEQ ID NO | TARGET SITE | SEQUENCE | SEQ ID NO |
|---|---|---|---|---|---|
| 153826 | 3' UTR | 4 | 4155 | tcttccatggtcagctgccc | 187 |
| 153827 | 3' UTR | 4 | 4165 | gggctctcaatcttccatgg | 188 |

The antisense compounds in Table 5 were tested for their ability to reduce STAT5A protein expression in the human TF-1 erythroleukemia cell line. TF-1 cells were cultured in RPMI 1640 medium supplemented with 10% heat-inactivated fetal bovine serum (Sigma-Aldrich, St.Louis, Mo.), 10 mM Hepes, pH 7.2, 50 µM 2-ME, 2 mM L-glutamine, 100 U/ml penicillin, 100 µg/ml streptomycin (all supplements from Invitrogen Corporation, Carlsbad, Calif.). ISIS 153814 (SEQ ID NO: 19) and ISIS 153820 (SEQ ID NO: 20) were also tested. $1 \times 10^7$ cells were transfected with 10 µM concentration of antisense oligonucleotides by electroporation (48 ohms, 1200 microFarads, 175 Volts), using a BTX electroporator (San Diego, Calif.). Cells electroporated in the presence of phosphate-buffered saline alone served as controls. Cells were harvested 48 hours following oligonucleotide treatment, and STAT5A protein levels were assessed using Western blot analysis.

Western blot analysis (immunoblot analysis) was carried out using standard methods. Cells were washed once with PBS, suspended in Laemmli buffer (100 µL/well), boiled for 5 minutes and loaded on an 8% SDS-PAGE gel. Gels were run for 1.5 hours at 150 V, and transferred to nitrocellulose for western blotting. Primary antibody directed to STAT5A was used (Upstate Biotechnology, Inc., Charlottesville, Va.) and visualized using enhanced chemiluminescence. Bands were visualized using a PHOSPHORIMAGER™ (Molecular Dynamics, Sunnyvale Calif.).

SEQ ID NOs 19, 20, 172, 173, 175, 176, 180, 181 and 182 were able to reduce STAT5A protein expression by at least 30%, demonstrating that the treatment of cultured cells with antisense compounds interferes with STAT5A protein expression.

Example 18

Antisense Inhibition of Human STAT5 Expression by Chimeric Phosphorothioate Oligonucleotides Having 2'-MOE Wings and a Deoxy Gap In a further embodiment, additional antisense compounds were designed to target different regions of the human STAT5B RNA, using published sequences for human STAT5B (GenBank accession number U48730.2, incorporated herein as SEQ ID NO: 151). "Target site" indicates the first (5'-most) nucleotide number on the particular target sequence to which the compound binds. The target site for both STAT5 isoforms is indicated for each antisense compound. If present, "–" indicates that no target site for a particular antisense compound is found in the referenced target sequence. All compounds in Table 6 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

TABLE 6

Chimeric oligonucleotides targeted to human STAT5A and STAT5B having 2'MOE wings and deoxy gaps

| | | STAT5B | | STAT5A | | | |
|---|---|---|---|---|---|---|---|
| ISIS # | REGION | TARGET SEQ ID NO | TARGET SITE | TARGET SEQ ID NO | TARGET SITE | SEQUENCE | SEQ ID NO |
| 168517 | Start codon | 151 | 1 | – | – | cacagccatggtttacccgg | 189 |
| 168518 | Coding | 151 | 87 | – | – | tgccgcacctcaatgggaaa | 190 |
| 168519 | Coding | 151 | 406 | – | – | ggacatggcatcagcaaggc | 191 |
| 168520 | Coding | 151 | 616 | 4 | 1246 | ctgcttctgctggagggccg | 192 |
| 168521 | Coding | 151 | 639 | 4 | 1269 | tgcaaccaggcctccagaga | 193 |
| 168522 | Coding | 151 | 698 | 4 | 1328 | tcttctggtgcttctcggcc | 194 |
| 168523 | Coding | 151 | 843 | 4 | 1473 | tcggccaacttctcacacca | 195 |
| 168524 | Coding | 151 | 927 | 4 | 1557 | atctcctccactgggccggg | 196 |
| 168525 | Coding | 151 | 1174 | – | – | gccactgtaatcattgcggg | 197 |
| 168526 | Coding | 151 | 1358 | – | – | ccagctcatttccaccaaca | 198 |
| 168527 | Coding | 151 | 1429 | – | – | cgtcgcattgttgtcctggc | 199 |
| 168528 | Coding | 151 | 1499 | 4 | 2129 | gcactttgtcaggcacggca | 200 |

TABLE 6-continued

Chimeric oligonucleotides targeted to human STAT5A and STAT5B having 2'MOE wings and deoxy gaps

| | | STAT5B | | STAT5A | | | |
|---|---|---|---|---|---|---|---|
| ISIS # | REGION | TARGET SEQ ID NO | TARGET SITE | TARGET SEQ ID NO | TARGET SITE | SEQUENCE | SEQ ID NO |
| 168529 | Coding | 151 | 1625 | 4 | 2255 | ggtggctgctgctgttgttg | 201 |
| 168530 | Coding | 151 | 1657 | — | — | ccaggacacagacaggccac | 202 |
| 168531 | Coding | 151 | 1661 | — | — | gggaccaggacacagacagg | 203 |
| 168532 | Coding | 151 | 1808 | — | — | ggtcatgggcctgttgcttg | 204 |
| 168533 | Coding | 151 | 1871 | — | — | tgccgccaatttctgagtca | 205 |
| 168534 | Coding | 151 | 1983 | — | — | ttcaagtctcccaagcggtc | 206 |
| 168535 | Coding | 151 | 1985 | — | — | aattcaagtctcccaagcgg | 207 |
| 168536 | Coding | 151 | 2014 | — | — | tggccgatcaggaaacacgt | 208 |
| 168537 | Coding | 151 | 2282 | — | — | ccattgtgtcctccagatcg | 209 |
| 168538 | Coding | 151 | 2331 | — | — | tgactgtccattggccggcc | 210 |
| 168539 | Coding | 151 | 2343 | — | — | tgcgggatccactgactgtc | 211 |
| 168540 | Stop codon | 151 | 2378 | — | — | tgaagatggagaggtcgcgg | 212 |
| 168541 | 3'UTR | 151 | 2512 | — | — | gccaccatgcacagaaacac | 213 |

The compounds in Table 6 were analyzed for their effect on STAT5A and STAT5B mRNA levels in Molt-4 cells. ISIS 153820 (SEQ ID NO: 20), which targets only human STAT5A, was used as a control for the inhibition of STAT5A. The human T lymphoblast cell line, Molt-4, was cultured in RPMI-1640 containing 10% fetal bovine serum, 1% L-glutamine, 10 mM Hepes, and $5 \times 10^{-5}$ M 2-mercaptoethanol (all culture reagents from Invitrogen Corporation, Carlsbad, Calif.). $1 \times 10^7$ cells were transfected with 10 μM concentration of antisense oligonucleotides by electroporation (48 ohms, 1200 microFarads, 175 Volts), using a BTX electroporator (San Diego, Calif.). Cells electroporated in the presence of phosphate-buffered saline alone served as controls. mRNA levels were monitored 16 hours following transfection. STAT5A and STAT5B expression levels were measured by quantitative real-time PCR as described in other examples herein. Data were normalized to control samples. If present, "–" indicates that no target site for a particular antisense compound is found in the referenced target sequence.

TABLE 7

Antisense inhibition of human STAT5B by chimeric oligonucleotides having 2' MOE wings and deoxy gaps

| | | STAT5B | | | STAT5A | | | |
|---|---|---|---|---|---|---|---|---|
| ISIS # | Region | TARGET SEQ ID NO | TARGET SITE | % INHIB | TARGET SEQ ID NO | TARGET SITE | % INHIB | SEQ ID NO |
| 153820 | 3' UTR | — | — | 0 | 4 | 3311 | 45 | 20 |
| 168517 | Start codon | 151 | 1 | 18 | — | — | 14 | 189 |
| 168518 | Coding | 151 | 87 | 56 | — | — | 0 | 190 |
| 168519 | Coding | 151 | 406 | 43 | — | — | 6 | 191 |
| 168520 | Coding | 151 | 616 | 28 | 4 | 1246 | 0 | 192 |
| 168521 | Coding | 151 | 639 | 12 | 4 | 1269 | 10 | 193 |
| 168522 | Coding | 151 | 698 | 66 | 4 | 1328 | 23 | 194 |
| 168524 | Coding | 151 | 927 | 81 | 4 | 1557 | 17 | 196 |
| 168525 | Coding | 151 | 1174 | 70 | — | — | 4 | 197 |
| 168526 | Coding | 151 | 1358 | 57 | — | — | 5 | 198 |
| 168527 | Coding | 151 | 1429 | 75 | — | — | 22 | 199 |
| 168528 | Coding | 151 | 1499 | 78 | 4 | 2129 | 59 | 200 |
| 168529 | Coding | 151 | 1625 | 50 | 4 | 2255 | 0 | 201 |
| 168530 | Coding | 151 | 1657 | 42 | — | — | 39 | 202 |
| 168531 | Coding | 151 | 1661 | 3 | — | — | 7 | 203 |
| 168532 | Coding | 151 | 1808 | 66 | — | — | 16 | 204 |

TABLE 7-continued

Antisense inhibition of human STAT5B by chimeric oligonucleotides having 2' MOE wings and deoxy gaps

| ISIS # | Region | STAT5B TARGET SEQ ID NO | TARGET SITE | % INHIB | STAT5A TARGET SEQ ID NO | TARGET SITE | % INHIB | SEQ ID NO |
|---|---|---|---|---|---|---|---|---|
| 168533 | Coding | 151 | 1871 | 83 | — | — | 21 | 205 |
| 168534 | Coding | 151 | 1983 | 49 | — | — | 22 | 206 |
| 168535 | Coding | 151 | 1985 | 39 | — | — | 3 | 207 |
| 168536 | Coding | 151 | 2014 | 69 | — | — | 11 | 208 |
| 168537 | Coding | 151 | 2282 | 65 | — | — | 4 | 209 |
| 168538 | Coding | 151 | 2331 | 70 | — | — | 50 | 210 |
| 168539 | Coding | 151 | 2343 | 75 | — | — | 19 | 211 |
| 168540 | Stop codon | 151 | 2378 | 30 | — | — | 20 | 212 |
| 168541 | 3' UTR | 151 | 2512 | 73 | — | — | 0 | 213 |

These data demonstrate that SEQ ID NOs 190, 191, 196, 197, 198, 201, 204, 205, 207, 208, 209, 211 and 213 exhibit greater than 40% inhibition of STAT5B and less than 20% inhibition of STAT5A.

What is claimed is:

1. An antisense compound 16, 17, 18, 19, 20, 21. 22, 23, 24 or 25 nucleobases in length targeted to a nucleic acid molecule encoding STAT5A (SEQ ID NO: 4) or STAT5B (SEQ ID NO: 151), wherein said compound has at least 80% identity with SEQ ID NO: 36.

2. The antisense compound of claim 1 which is 18, 19,20, 21 or 22 nucleobases in length and has at least 90% identity with SEQ ID NO: 36.

3. The antisense compound of claim 2 which is 19, 20 or 21 nucleobases in length and has at least 95% identity with SEQ ID NO: 36.

4. The antisense compound of claim 1 which is a chimeric antisense compound.

5. The antisense compound of claim 1 comprising at least one modified internucleoside linkage, sugar moiety, or nucleobase.

6. The antisense compound of claim 1 comprising at least one 2'-O-methoxyethyl sugar moiety.

7. The antisense compound of claim 1 comprising at least one phosphorothioate internucleoside linkage.

8. The antisense compound of claim 1 wherein at least one cytosine is a 5-methylcytosine.

* * * * *

UNITED STATES PATENT AND TRADEMARK OFFICE
CERTIFICATE OF CORRECTION

PATENT NO. : 7,176,303 B2
APPLICATION NO. : 10/704263
DATED : February 13, 2007
INVENTOR(S) : Susan M. Freier and James Karras It is certified that error appears in the above-identified patent and that said Letters Patent is hereby corrected as shown below:

Title Page:
Item [56], Col. 2, line 12,
References Cited, OTHER PUBLICATIONS, "Carlesso" reference, please delete "phosporylation" and insert therefor --phosphorylation--;

Title page:
Item (56), col. 2, line 37,
"Grimley" reference, delete "Statb:" and insert therefor --Stat5b:--;

Column 133, Claim 1, line 29, delete "." and insert therefor --,--.

Signed and Sealed this

Tenth Day of April, 2007

JON W. DUDAS
*Director of the United States Patent and Trademark Office*